(12) United States Patent
Katra et al.

(10) Patent No.: US 10,376,184 B2
(45) Date of Patent: Aug. 13, 2019

(54) APPARATUS AND METHOD FOR PATIENT ACTIVITY ESTIMATION AND CLASSIFICATION

(71) Applicant: Greatbatch Ltd., Clarence, NY (US)

(72) Inventors: Rodolphe Katra, Blaine, MN (US); Niranjan Chakravarthy, Eden Prairie, MN (US)

(73) Assignee: Greatbatch Ltd., Clarence, NY (US)

( * ) Notice: Subject to any disclaimer, the term of this patent is extended or adjusted under 35 U.S.C. 154(b) by 1066 days.

(21) Appl. No.: 14/200,550

(22) Filed: Mar. 7, 2014

(65) Prior Publication Data

US 2014/0257115 A1 Sep. 11, 2014

Related U.S. Application Data

(60) Provisional application No. 61/775,081, filed on Mar. 8, 2013.

(51) Int. Cl.
| | |
|---|---|
| *A61B 5/11* | (2006.01) |
| *A61B 5/04* | (2006.01) |
| *A61B 5/0402* | (2006.01) |
| *A61B 5/00* | (2006.01) |
| *A61B 5/0428* | (2006.01) |
| *A61B 5/0452* | (2006.01) |
| *A61N 1/362* | (2006.01) |

(52) U.S. Cl.
CPC .............. *A61B 5/1118* (2013.01); *A61B 5/04* (2013.01); *A61B 5/0402* (2013.01); *A61B 5/0428* (2013.01); *A61B 5/0452* (2013.01); *A61B 5/1123* (2013.01); *A61B 5/7207* (2013.01); *A61B 5/4809* (2013.01); *A61N 1/362* (2013.01)

(58) Field of Classification Search
None
See application file for complete search history.

(56) References Cited

U.S. PATENT DOCUMENTS 7,769,436 B1 * 8/2010 Boileau .............. A61N 1/36585
600/509
8,180,442 B2 5/2012 Belalcazar et al.
(Continued)

FOREIGN PATENT DOCUMENTS

WO WO2004093676 11/2004
WO WO2006054306 5/2006

OTHER PUBLICATIONS

Search Report from EP Application No. 14158387.2 dated May 20, 2014, 7 pages.

*Primary Examiner* — Michael R Bloch
(74) *Attorney, Agent, or Firm* — Hollingsworth Davis, LLC

(57) ABSTRACT

A medical device includes a housing and an electrode arrangement coupled to the housing and configured to sense an electrical physiologic signal from a patient. The device also includes detection circuitry coupled to the electrode arrangement and configured to obtain a cardiac signal component and a non-cardiac signal component from the physiological signal. A processor is coupled to the detection circuitry. The processor is configured to detect patient activity using at least the non-cardiac signal component and discriminate between voluntary and involuntary activity of the patient based on a comparison of temporally aligned cardiac and non-cardiac signal components.

19 Claims, 16 Drawing Sheets

(56) References Cited

U.S. PATENT DOCUMENTS

| | | |
|---|---|---|
| 2005/0256418 A1 | 11/2005 | Mietus et al. |
| 2009/0156908 A1* | 6/2009 | Belalcazar ........... A61B 5/0031 600/301 |
| 2009/0264783 A1* | 10/2009 | Xi ......................... A61B 5/046 600/518 |

* cited by examiner

APPARATUS AND METHOD FOR PATIENT ACTIVITY ESTIMATION AND CLASSIFICATION

RELATED APPLICATIONS

This application claims the benefit of Provisional Patent Application Ser. No. 61/775,081, filed on Mar. 8, 2013, to which Applicant claims priority under 35 U.S.C. § 119(e), and which is incorporated herein by reference in its entirety.

TECHNICAL FIELD

This patent document pertains generally to disease monitoring and more particularly, but not by way of limitation, to using patient physical activity as an indicator for disease monitoring.

BACKGROUND

Electrical signals cause a heart to beat. In a healthy patient, regular heart beats pump blood through the cardiovascular system. The human cardiovascular system is responsible for receiving oxygen-deprived blood into the heart from the venous system of the body, delivering the oxygen-deprived blood to the lungs to be replenished with oxygen, receiving the oxygenated blood from the lungs back into the heart, and delivering the oxygenated blood to the body via the arterial vasculature. This process is regulated within the heart by electrical pulses that control operation of the heart's receiving and pumping chambers.

In a healthy heart, the sinoatrial node of the heart generates electrical pulses in a consistent and regulated fashion to regulate receiving and pumping blood in the heart's chambers. The electrical impulses propagate as activation wavefronts across the atria, the upper chambers of the heart, and cause cells of the atria to depolarize and contract, which forces blood from the atria to the ventricles, the lower chambers of the heart. The ventricles receive the blood from the atria, and the wavefront, after passing through the atrioventricular node and moving to the Purkinje system, moves to cells of the ventricles causing the ventricles to contract and pump the blood to the lungs and to the rest of the body.

Various aspects of cardiac activity (e.g., heart rate, arrhythmias) can be detected by measuring, recording, and analyzing cardiac electrical signals, such as an electrocardiogram (ECG) signal. One way of measuring ECG signals involves attaching electrodes, typically ten, externally to a patient's skin and sensing the electrical signals that form the ECG waveform.

Implantable monitoring systems can be implanted under the skin with electrodes that sense subcutaneous electrical signals, including ECG signals, which are analyzed as being indicative of cardiac activity. In such systems, the electrodes also receive extraneous non-cardiac electrical signal information, which is typically filtered out to produce a more readable ECG. Non-cardiac electrical signals can be generated by muscle tissues during physical activity, for example. In some examples, an implantable loop recorder (ILR) can record and quantify patient heart electrical activity.

SUMMARY

Embodiments of the disclosure are directed to methods and devices for assessing a patient using a multiplicity of signal components derived from a common physiologic signal acquired from the patient. According to some embodiments, a method of assessing a patient involves sensing an electrical physiologic signal between a single electrode pair, obtaining a cardiac signal component from the physiological signal, and obtaining a non-cardiac signal component from the physiologic signal. The method also involves comparing the cardiac and non-cardiac signal components to thresholds established for the patient, and detecting patient activity using at least the non-cardiac signal component. The method further involves discriminating between voluntary and involuntary activity of the patient based on the comparison and temporal alignment of the cardiac signal component relative to the non-cardiac signal component.

According to other embodiments, a method of assessing a patient involves sensing an electrical physiologic signal between a single electrode pair, obtaining a cardiac signal component from the physiological signal, and deriving a cardiac metric using the cardiac signal component. The method also involves obtaining a non-cardiac signal component from the physiologic signal, deriving an activity metric using the non-cardiac signal component, and comparing the cardiac and activity metrics. The method further involves discriminating between voluntary and involuntary activity of the patient based on the comparison and temporal alignment of the cardiac and activity metrics.

In accordance with some embodiments, a medical device includes a housing, and an electrode arrangement coupled to the housing and configured to sense an electrical physiologic signal from a patient. The device also includes detection circuitry coupled to the electrode arrangement and configured to obtain a cardiac signal component and a non-cardiac signal component from the physiological signal. A processor is coupled to the detection circuitry. The processor is configured to detect patient activity using at least the non-cardiac signal component and discriminate between voluntary and involuntary activity of the patient based on a comparison of temporally aligned cardiac and non-cardiac signal components.

The above summary is not intended to describe each disclosed embodiment or every implementation of the present disclosure. The figures and the detailed description below more particularly exemplify illustrative embodiments

BRIEF DESCRIPTION OF THE DRAWINGS

Throughout the specification reference is made to the appended drawings, where like reference numerals designate like elements, and wherein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
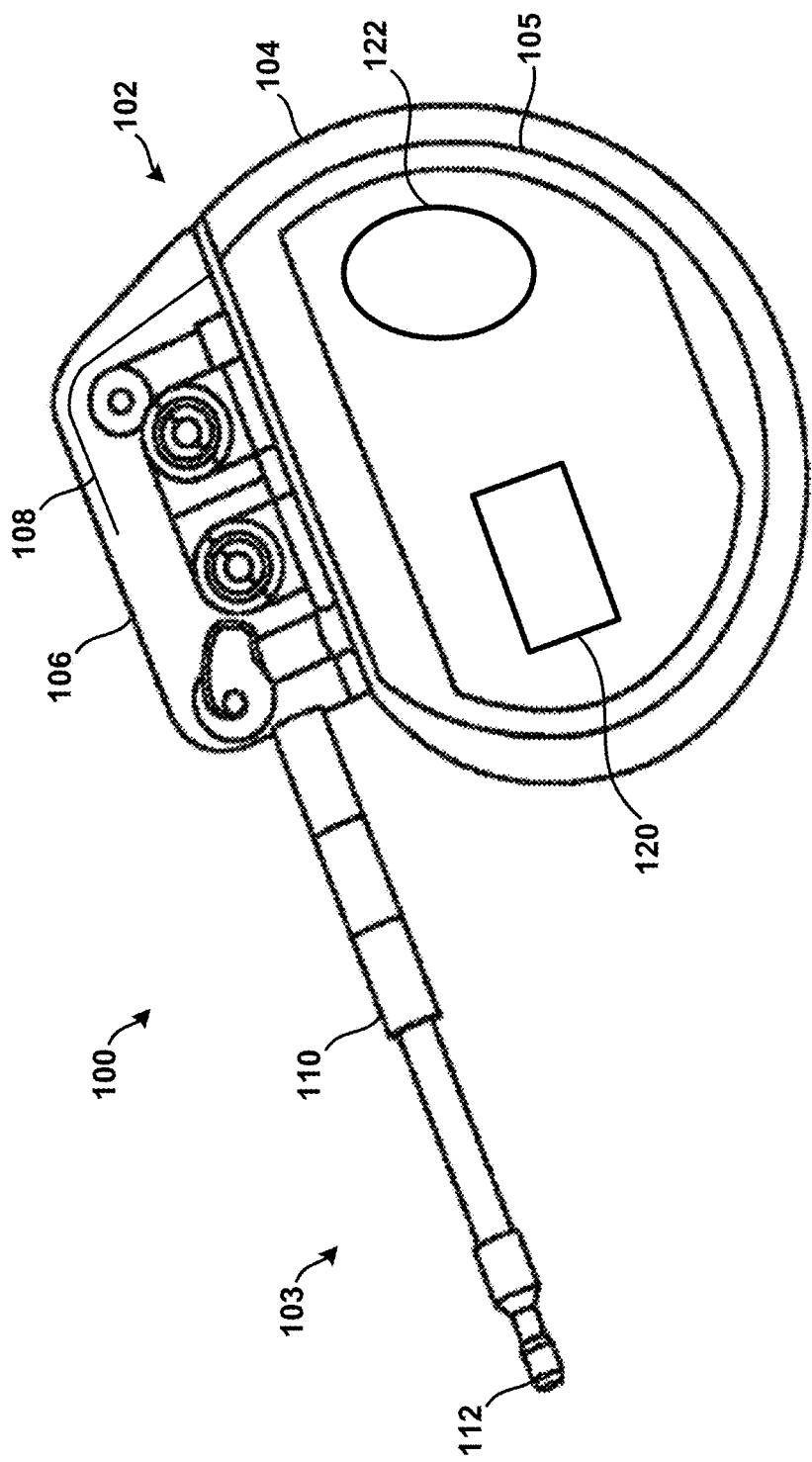
FIG. 1 illustrates a representative implantable device that can be subcutaneously implanted under a patient's skin, typically in a pectoral region of a patient's thorax, in accordance with various embodiments.

The present inventors have recognized, among other things, that patient physical activity is a measure for disease monitoring. The present inventors have further recognized that it is desirable to provide a device or method for remotely monitoring or actively interrogating patient activity levels.

In the following detailed description, the examples are described in sufficient detail to enable those skilled in the art to practice the invention, and it is to be understood that other examples may be utilized and that structural changes may be made without departing from the scope of the present invention. Therefore, the following detailed description is not to be taken in a limiting sense.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, or process that includes elements in addition to those listed after such a term are still deemed to fall within the scope of the description. Moreover, the terms "first," "second," and "third," etc. are used merely as labels, and are not intended to impose numerical requirements on their objects.

In some embodiments, a patient monitoring device, such as an implantable loop recorder (ILR), measures ECG in real-time. Currently, the beat-detection values are of interest. In addition to cardiac activity, the measured signal(s) also have additional information corresponding to patient activity, such as EMG (muscle activity). Using a signal separation (e.g., frequency domain filtering or wavelet decomposition), the measured ECG signal can be split into several components. The high frequency components may correspond to muscle activity (e.g., voluntary upper-chest movement) and the low frequency components (e.g., drifts) could arise from patient movements (e.g., respiration). Thus, the low and high frequency and the non-ECG (i.e., PQRST) signal components can be used to determine the presence and quantify patient activity levels. The use of high-frequency band-pass filtered signal components as a measure for activity is described in U.S. Pat. No. 8,180,442, which is incorporated by reference herein.

In some examples, the quantification and detection of patient activity can be performed on the periodic, asymptomatic, or symptomatic ECG strips acquired during normal patient monitoring device (e.g., ILR) operation or extended to the measured ECG in real-time for all time instances.

In some examples, an extension of the activity measurement method is discriminating between transient/involuntary patient activity (e.g., coughing) versus sustained patient activity (e.g., running). In various examples, the discrimination can be performed in an open-loop or closed-loop manner. In the open-loop setting, in some examples, patient activity can be classified as transient (vs. sustained) if (i) it occurs during sleep (vs. active) as determined by the heart-rate and breath-rate level and frequency components, (ii) short (vs. long) duration of non-cardiac activity signal components, and (iii) low (vs. high) power (e.g., measured as the product of intensity and duration of activity) activity.

In the closed-loop setting, in some examples, the patient/caregiver/associate/clinic can input timing and levels (e.g., measured with other devices such as accelerometers or actigraphs) of one or more periods of the patient's sustained and voluntary activity (e.g., running), before, after or during the activity instances. The input can happen on the external accessory that is paired to the implantable device, on the remote web-server that receives data wirelessly or the resulting report generated from an analysis of the non-ECG data, or on all. This provides a patient-specific closed-loop activity measurement tuning method where, e.g., the quantified activity signal components during the said activity periods can be used to derive patient-specific threshold (duration/intensity/power) and activity signal signatures and patterns. If, in some examples, the activity signal components (during subsequent monitoring) meet or exceed the thresholds, then the patient activity is classified as sustained; otherwise, it is classified as transient. Such a feedback adaptive scheme can also be used, in some examples, to train the system to transient activity. Such a method makes the activity level tracker patient-specific.

For instance, while the patient activity content isolated from the total recorded ECG signal can be used in isolation for assessment of the patient status, an aspect of the present subject matter is the interpretation of the patient activity content relative to the ECG content, derived from the same signal. The dynamic relationship between the activity content and ECG content is important is achieving an accurate and applicable patient assessment. While each has value in its own regards, the interplay between the two signals allows for a more comprehensive assessment of patient condition. For example, an elevated patient activity intensity in the context of an elevated patient heart rate can indicate compensated heart function, whereas a low patient activity intensity with an elevated heart rate can indicate an uncompensated arrhythmia. Conversely, a low patient activity intensity with a low heart rate can indicate normal patient status, whereas a low heart rate with a high activity intensity can indicate an inadequate cardiac chronotropic function, epileptic seizures, or other. These examples are merely illustrative, and not restrictive, of how the interpretation of the patient activity and the ECG derived from the same signal could be used to assess patient function. Other applications and interpretations are possible and are contemplated herein.

In some examples, temporal interpretation is possible based upon the simultaneous occurrence of these derived measures since they are derived from the same signal. In some examples, individual ECG strips can be used to present point-wise activity estimates, or multiple ECG strips can be used to temporally trend patient activity. In some examples, false positive activity detections can be mitigated by viewing adjacent activity strips as well. In some examples, activity measures from multiple implanted or non-implanted devices can be used to qualify "local" (e.g., chest alone) vs. "global" (upper and lower torso) patient activity.

Various embodiments disclosed herein use existing ECG measurements (e.g., antenna to 'can') to quantify patient activity. In further examples, in general with implantable devices and specifically with the ILR devices, such devices can measure the signals from the suture points to antenna and/or from the suture points to can. With the suture points intended to 'hold' the device in place, in some examples, they can be used as reference to measure the deviations from the rest of the device. In still further examples, such measurement schemes can be extended to other implantable and non-implantable devices whose functioning depends on an anchored location (e.g., ICD/CRT).

At least some of the embodiments described herein indirectly measure patient activity. In further examples, patient activity can also be explicitly monitored with on-board accelerometers (multi-axis models for patient orientation as well).

Although described herein with respect to devices using ECG, in other examples, other measurement systems, including EMG, etc., can be used. Although described herein with reference to an ILR, the presently-described examples can be used in other implanted measurement systems (e.g., ICD/CRT, pacemakers) or other surface (patient-external) measurement systems. These and other similar devices are collectively referred to herein as a patient monitoring device, understanding that such a device may include a therapy delivery capability according to various embodiments.

Figure 2:
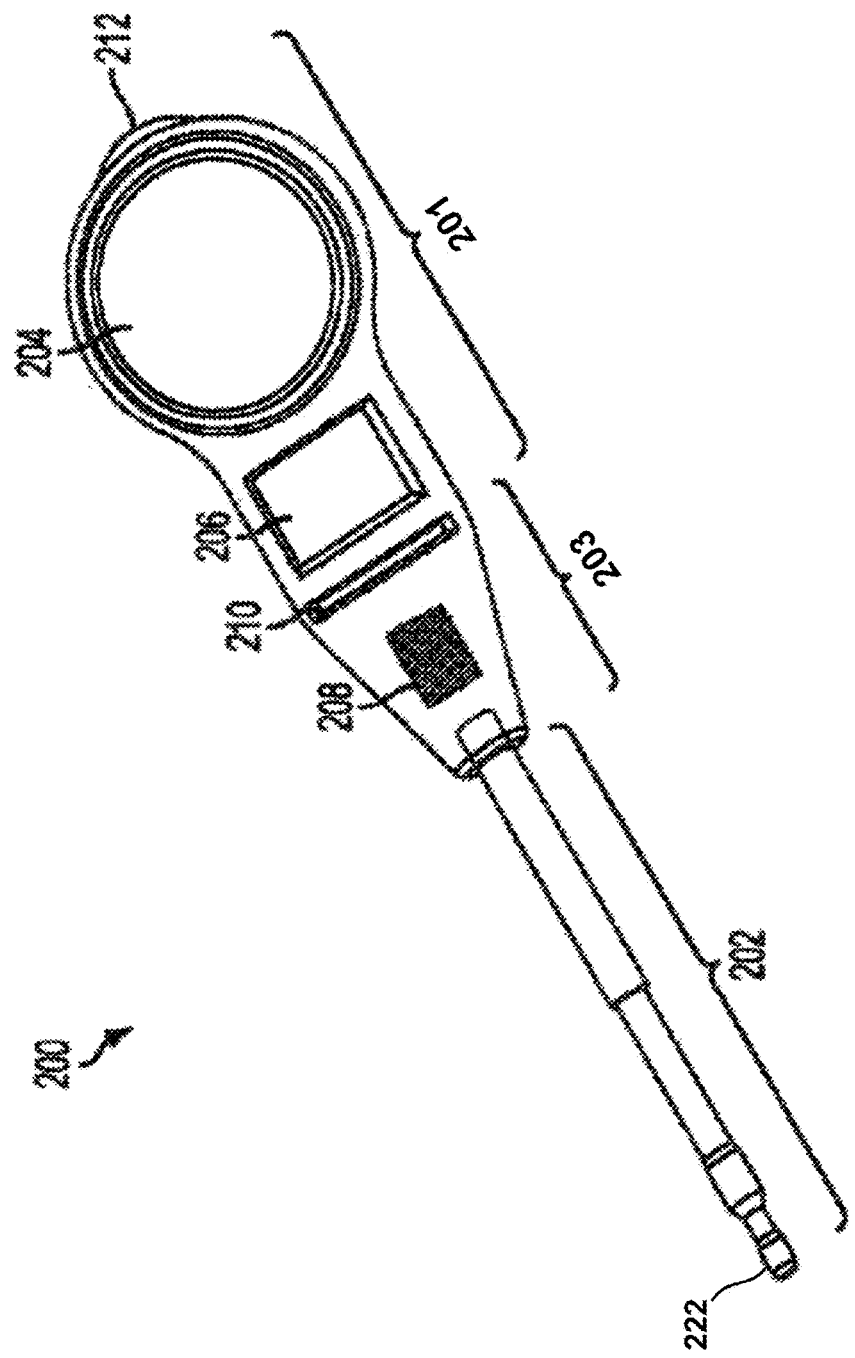
FIG. 2 illustrates a representative implantable device that can be subcutaneously implanted under a patient's skin in accordance with other embodiments.

In accordance with various embodiments, a patient monitoring device may be implemented as an implantable loop recorder, which may be leadless or may include one or more subcutaneous leads. Two representative embodiments of such a patient monitoring device are illustrated in FIGS. 1 and 2. Each of the patient monitoring devices illustrated in FIGS. 1 and 2 is configured to record an electrical physiologic signal, such as an EGG signal for the patient, from which various diagnostic information can be derived. It is understood that the devices illustrated herein are disclosed for illustrative purposes, and that methods and apparatuses of the present disclosure may be implemented in a variety of implantable and external embodiments.

FIG. 1 illustrates a representative patient monitoring device 100 that can be subcutaneously implanted under a patient's skin, typically in a pectoral region of a patient's thorax, in accordance with various embodiments. The device 100 may be a minimally invasive implantable monitoring device that senses and records a physiologic parameter, such as electrical activity of the heart, within a body of a patient. In some implementations, the device 100 is an implantable monitoring device that senses and records a physiologic parameter, such as an ECG signal, within the body of the patient and wirelessly transmits information associated with the physiologic parameter to an external device or system. Such a monitoring-only device that records cardiac electrical information may be implanted in a human patient for a relatively short period of time, such as a few months for example.

Other physiologic parameters or combinations of parameters, such as other electrical physiologic signals (e.g., EMG signal, bio-impedance signal), mechanical signals (e.g., blood pressure signal, blood flow signal, pulse oximetry), chemical signals (e.g., glucose), temperature and the like may similarly be recorded by the device 100 in various implementations. The description that follows will focus without limitation on implementations where the device 100 is used to monitor a subcutaneous ECG signal, but in other implementations such monitoring could be combined with or substituted by other monitoring functions.

The implantable device 100 shown in FIG. 1 includes a proximal section 102 and a distal section 103. The proximal section 102 includes a housing 104 within which various components of the device 100 are disposed, including electronic circuitry 120 and a battery 105, which may be single-use or rechargeable in various implementations. The housing 104 may be configured to include one or more electrodes, an example of which is shown as electrode 122. All or a portion of the housing 104 may be configured as an "active can," and may further include an indifferent electrode (not shown) which is electrically isolated from the housing electrode(s) 122. A header 106 is connected to the housing 104 and to a distal extension 110, which is generally flexible or shapeable. A distal electrode 112 is disposed at a distal end of the extension 110. The header 106 serves to electrically couple the distal electrode 112 and any other electrical or optical component of the distal extension 110 with components within the housing 104 (e.g., electronic circuitry 120). An antenna 108 is shown extending from the housing 104 and into the header 108. The antenna 108 is configured for telemetering data from the implantable device 100, and can be configured to effect bi-directional wireless communication with a patient-external device or system. In some embodiments, the antenna 108 can be incorporated into the distal extension 110.

FIG. 2 illustrates a representative patient monitoring device 200 that can be subcutaneously implanted under a patient's skin, typically in a pectoral region of a patient's thorax, in accordance with other embodiments. The representative device 200 generally includes three sections: a proximal section 201, a distal extension 202, and a midsection 203 between the proximal section 201 and the distal extension 202. The proximal section 201 is configured to hermetically house a battery 204, which may be single-use or rechargeable in various implementations, and electronic circuitry 206 (e.g., an electronics module) for performing actions consistent with the device's intended purpose. Without limitation, examples of actions that may be performed with some implementations of the device 200 include measuring one or more physiologic signals, storing the measured signal (s) in memory within the device 200, processing collected data, and wirelessly transmitting or receiving information to/from an external device, among others.

The midsection 203 may include a non-hermetic external surface, and may be designed to enclose or embed components suited for housing in a non-conductive enclosure, such as components that communicate by field or wave properties that may otherwise be impeded by a conductive housing. In this implementation, the midsection 203 houses an antenna 208 for wirelessly transmitting data to an external device or wirelessly receiving data from an external device. In some implementations, the midsection 203 can include a charging coil (not shown) that can be excited (e.g., with an external charging coil placed in proximity to the implant location) to recharge a rechargeable battery 204 of the device 200. Hermetic feedthroughs 210 may be provided where electrical connections enter or exit the hermetic proximal section 201 from the non-hermetic midsection 203 to maintain hermeticity of the proximal section 201.

The distal extension 202 may be a flexible subcutaneous lead attached to the midsection 203 at one end. Lead 202 may include one or more electrodes, such as distal electrode 222, for measuring electrical activity or stimulating body tissue. In some implementations, the distal extension 202 can serve as the telemetry antenna for the device 200, and in these cases the depicted antenna 208 may be omitted. In some implementations, the telemetry antenna function is incorporated into the distal extension (lead) 202 independent from any ECG sensing lead functionality. The device 200 may include a feature on an exterior surface to facilitate grasping of the device 200 during extraction. For example, a retraction loop 212 near the proximal end 201 of the device 200 may be grasped or hooked in this fashion for ease of retraction. The loop 212 may in addition, or in the alternative, be configured as a suture hole to facilitate anchoring of the device 200 via a suture.

The devices 100 and 200 shown in FIGS. 1 and 2 may include one or more electrodes for electrically interfacing to surrounding tissue for the purpose of sensing electrical activity. In some implementations, devices 100 and 200 include two electrodes, such as a proximal electrode and a distal electrode, and may measure a potential difference (e.g., a subcutaneous ECG signal) between the proximal and distal electrodes. The electrodes may be located on the devices 100 and 200 to increase (e.g., maximize) signal vector length of a measured physiologic signal. In general, measured amplitude of a sensed physiologic signal, such as an ECG signal, will vary with device placement and orientation within the patient. Sensed signal amplitude may also be related to separation distance between the measuring electrodes. Positioning the proximal and distal electrodes near opposing ends (e.g., near opposite longitudinal ends) of the devices 100 and 200 can increase (e.g., maximize) the amplitude of the sensed physiologic signal for a given device length, which may lead to better measurement results. In other implementations, the devices 100 and 200 can include three electrodes, though any suitable number (one, two, three, four, five, etc.) may be used in other implementations. In some implementations, one or more of the electrodes of the devices 100 and 200 may comprise excitation electrodes or combination excitation/sense electrodes. By way of example, the devices 100 and 200 may measure a bio-impedance for diagnostic purposes by injecting a known current between two electrodes and measuring a resulting voltage between two electrodes.

Figure 3:
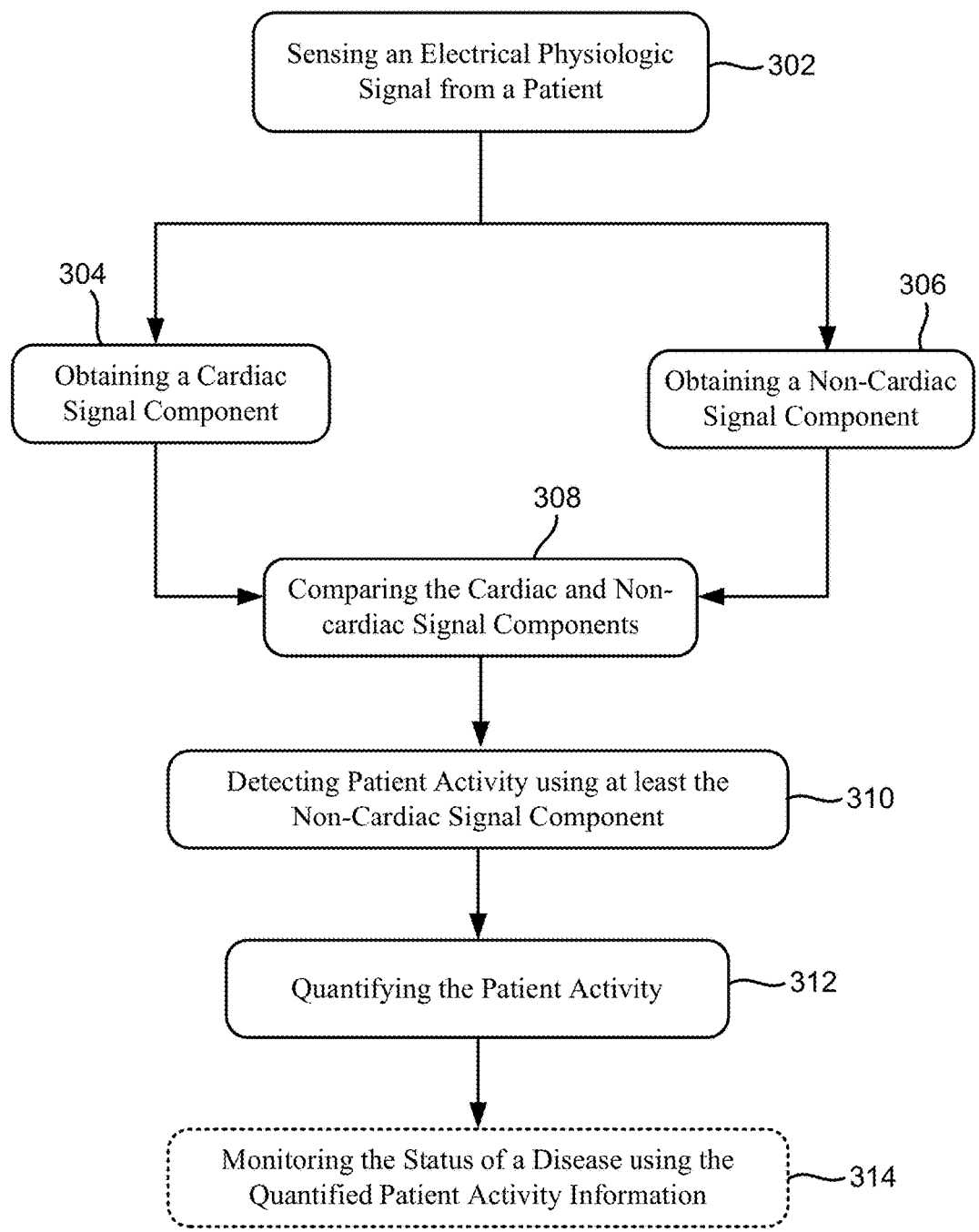
FIG. 3 illustrates a method of assessing patient status in accordance with various embodiments.

Turning now to FIG. 3, there is illustrated a method of assessing patient status in accordance with various embodiments. The methodology shown in FIG. 3 and other figures can be implemented by a patient monitoring device according to various embodiments. The methodology shown in FIG. 3 involves sensing 302 an electrical physiologic signal from a patient, such as a signal sensed from a subcutaneous, intra-thoracic, or cutaneous location. The sensed electrical physiologic signal is processed to obtain 304 a cardiac signal component and to obtain 306 a non-cardiac signal component. The cardiac signal component may include an ECG signal, for example. The non-cardiac signal component may include an activity signal indicative of muscle movement, for example. A comparison 308 is performed on the cardiac and non-cardiac signal components. In some embodiments, the cardiac and non-cardiac signal components are compared to respective thresholds, such as thresholds developed for the specific patient or for a population of patients. The thresholds may be developed and refined dynamically during real time monitoring of the patient by the patient monitoring device or by an external processor, for example.

In various embodiments, the interplay between the cardiac and non-cardiac signal components is evaluated to provide a more comprehensive assessment of the patient's condition. Evaluating the interplay between the two signal components may involve comparing each component to its respective threshold(s) as well as comparing one or more features of the two signal components relative to one another. Illustrative examples of patient assessment based on the interplay of cardiac and non-cardiac signal components are provided hereinbelow. The methodology shown in FIG. 3 further involves detecting 310 patient activity using at least the non-cardiac signal component, and quantifying 312 the patient activity. The methodology shown in FIG. 3 may further involve monitoring 314 the status of a patient's disease, including improvement, worsening and/or progression of a particular disease.

Figure 4:
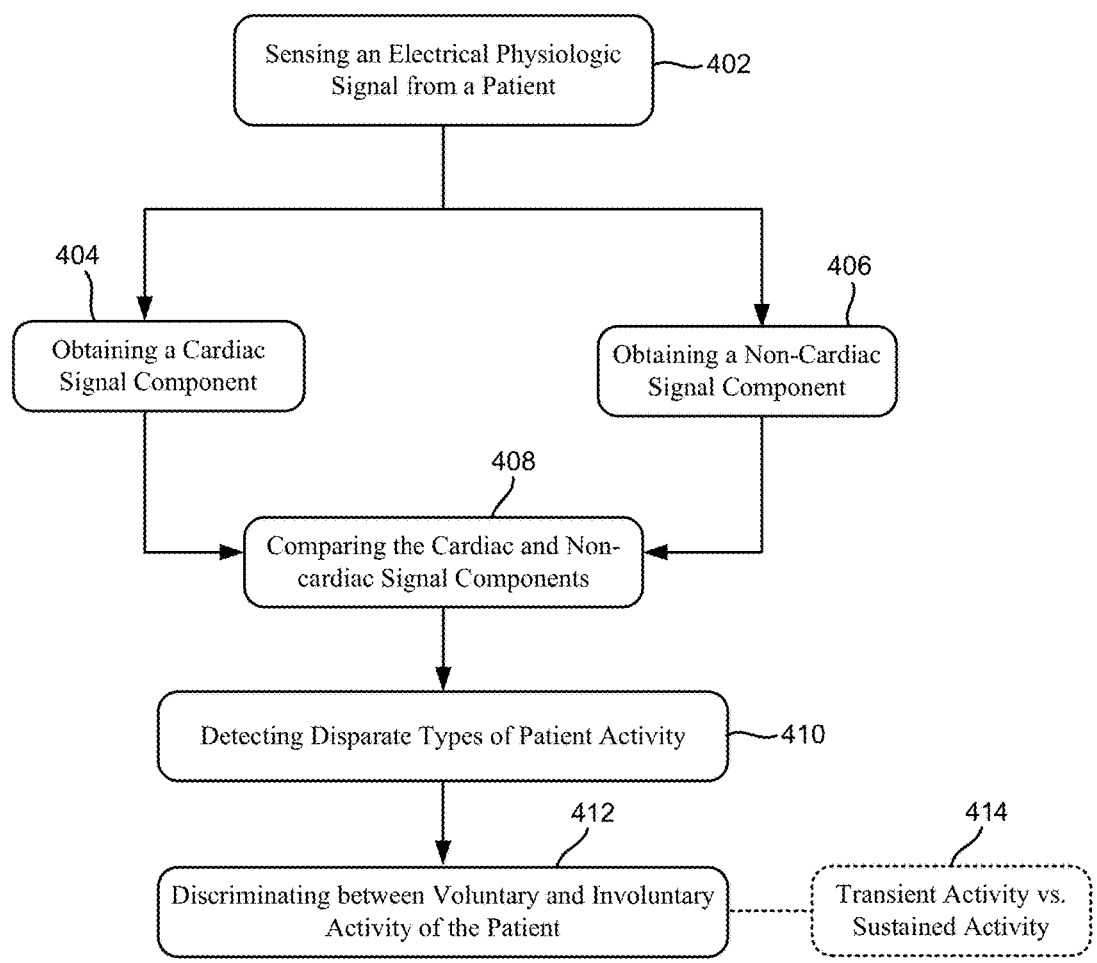
FIG. 4 illustrates a method of assessing patient status in accordance with other embodiments.

FIG. 4 illustrates a method of assessing patient status in accordance with other embodiments. The methodology shown in FIG. 4 involves sensing 402 an electrical physiologic signal from a patient, such as a signal sensed from a subcutaneous, intra-thoracic, or cutaneous location. The sensed electrical physiologic signal is processed to obtain 404 a cardiac signal component and to obtain 406 a non-cardiac signal component. The cardiac signal component may include an ECG signal, for example, and the non-cardiac signal component may include an activity signal indicative of muscle movement, for example. A comparison 408 is performed on the cardiac and non-cardiac signal components, such as comparisons with respective thresholds and/or comparisons between features of the two signal components that reveal interrelationships between the two signal components as discussed previously. The methodology shown in FIG. 4 further involves detecting 410 disparate types of patient activity based on the comparison of cardiac and non-cardiac signal components. The methodology of FIG. 4 also involves discriminating 412 between voluntary and involuntary activity of the patient based, for example, on an assessment of the interplay between the cardiac and non-cardiac signal components. Discriminating 412 between voluntary and involuntary activity of the patient may further involve discriminating 414 between transient activity and sustained activity of the patient. Illustrative examples of distinguishing between voluntary and involuntary activity of a patient using temporally related cardiac and non-cardiac signal components derived from the same electrical physiologic signal are provided hereinbelow.

Figure 5:
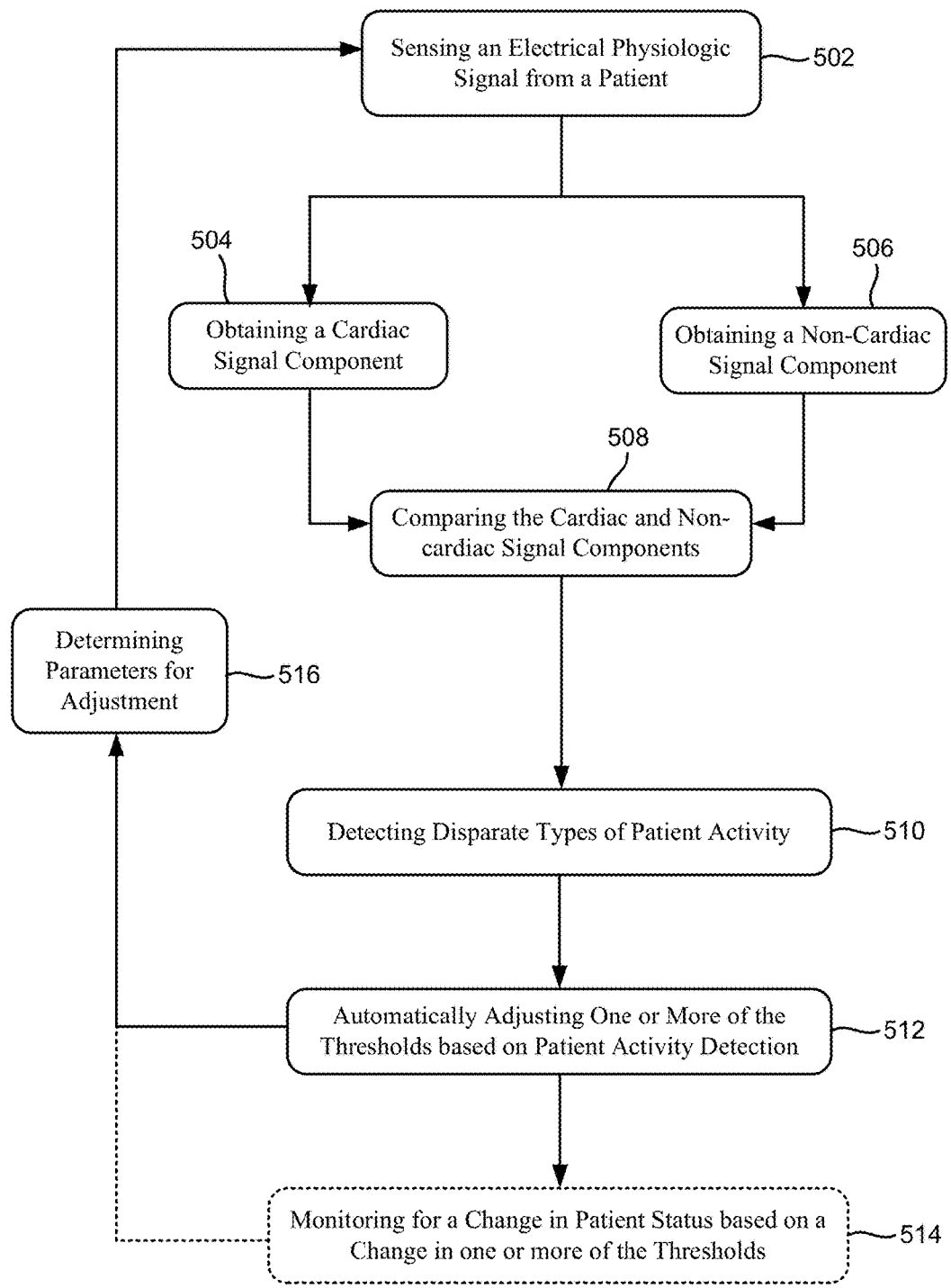
FIG. 5 illustrates a method of assessing patient status in accordance with some embodiments.

FIG. 5 illustrates a method of assessing patient status in accordance with various embodiments. The methodology shown in FIG. 5 involves sensing 502 an electrical physiologic signal from a patient, such as a signal sensed from a subcutaneous, intra-thoracic, or cutaneous location. The sensed electrical physiologic signal is processed to obtain 504 a cardiac signal component and to obtain 506 a non-cardiac signal component. The cardiac signal component may include an ECG signal, for example, and the non-cardiac signal component may include an activity signal indicative of muscle movement, for example. A comparison 508 is performed on the cardiac and non-cardiac signal components, such as comparisons with respective thresholds and/or comparisons between features of the two signal components that reveal interrelationships between the two signal components as discussed previously.

The methodology shown in FIG. 5 further involves detecting 510 disparate types of patient activity based on the comparison of cardiac and non-cardiac signal components. The methodology of FIG. 5 also involves automatically adjusting 512 one or more thresholds to which one or both of the cardiac and non-cardiac signal components are compared, and can further involve determining 516 device parameters for adjustment. For example, one or more activity thresholds can be initially established and then adjusted 512 over time (e.g., automatically or algorithmically by the monitoring device) based on detected patient activity over time. In some implementations, process flow from block 516 can pass to block 510 rather than (or in addition to) passing to block 502, depending on whether the signal needs to be collected de novo using the new parameters or reprocessing the same data with new parameters. The methodology illustrated in FIG. 5 can also involve monitoring 514 (optionally) for a change in patient status (e.g., activity status, disease status) based on change in one or more of the thresholds, and determining 516 parameters for adjustment. The adjusted parameters can be used in subsequent comparing 508, detecting 510, and adjusting 512 processes shown in FIG. 5.

Figure 6:
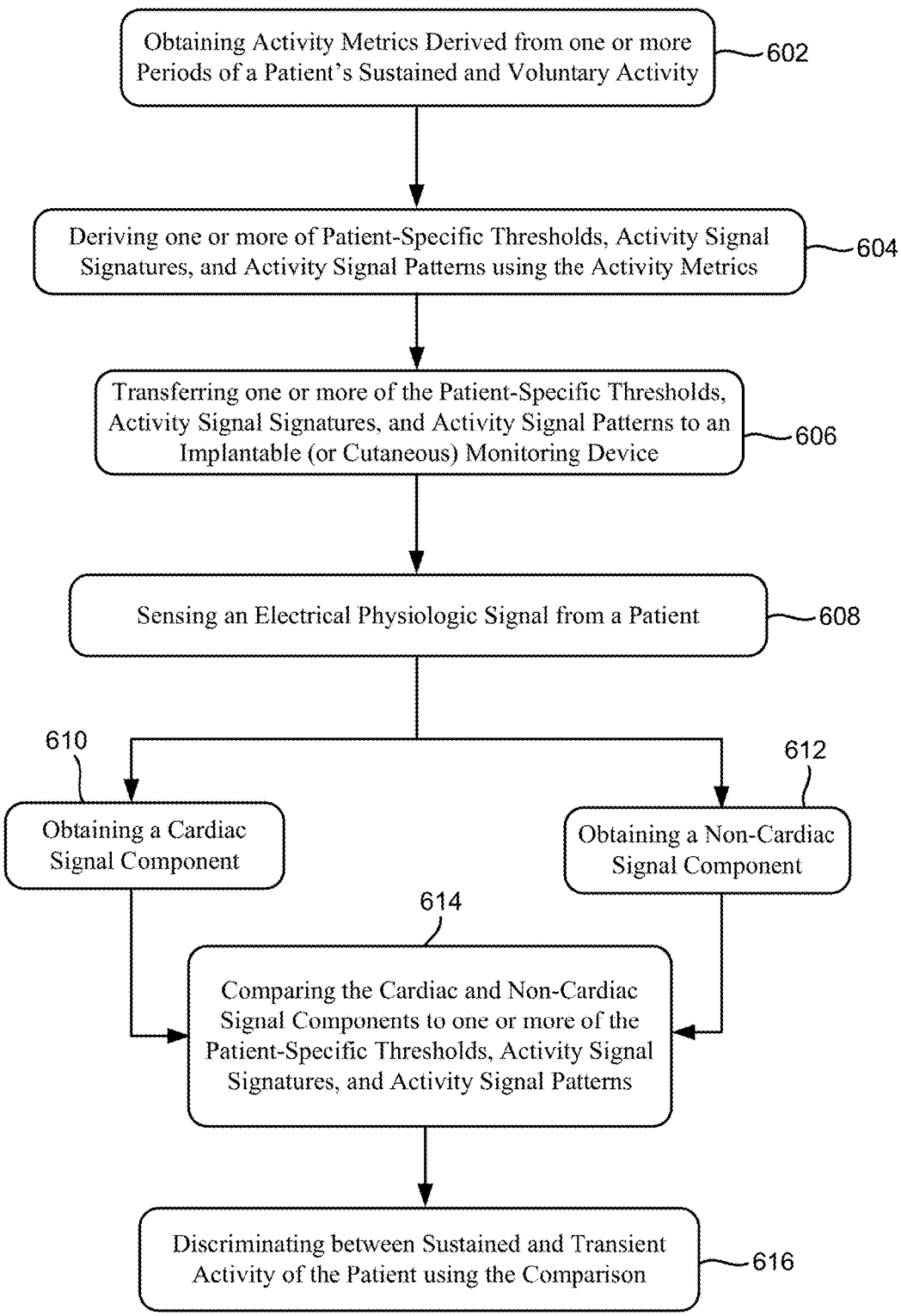
FIG. 6 illustrates a method of assessing patient status in accordance with various embodiments.

FIG. 6 illustrates a method of assessing patient status in accordance with various embodiments. The methodology shown in FIG. 6 involves obtaining 602 activity metrics derived from one or more periods of a patient's sustained and voluntary activity. The methodology illustrated in FIG. 6 also involves deriving 604 one or more of patient-specific thresholds, activity signal signature, and activity signal patterns using the activity metrics. The methodology further involves transferring 606 one or more of the patient-specific thresholds, activity signal signature, and activity signal patterns to an implantable or cutaneous patient monitoring device. Using the patient monitoring device, an electrical physiologic signal of the patient is sensed 608, from which cardiac and non-cardiac signal components are respectively obtained 610, 612. The cardiac signal component may include an ECG signal, for example, and the non-cardiac signal component may include an activity signal indicative of muscle movement, for example. The cardiac and non-cardiac signal components are compared 614 to one or more of the patient-specific thresholds, activity signal signature, and activity signal patterns using the activity metrics. The methodology shown in FIG. 6 further involves discriminating 616 between sustained and transient activity of the patient using the comparison.

Figure 7:
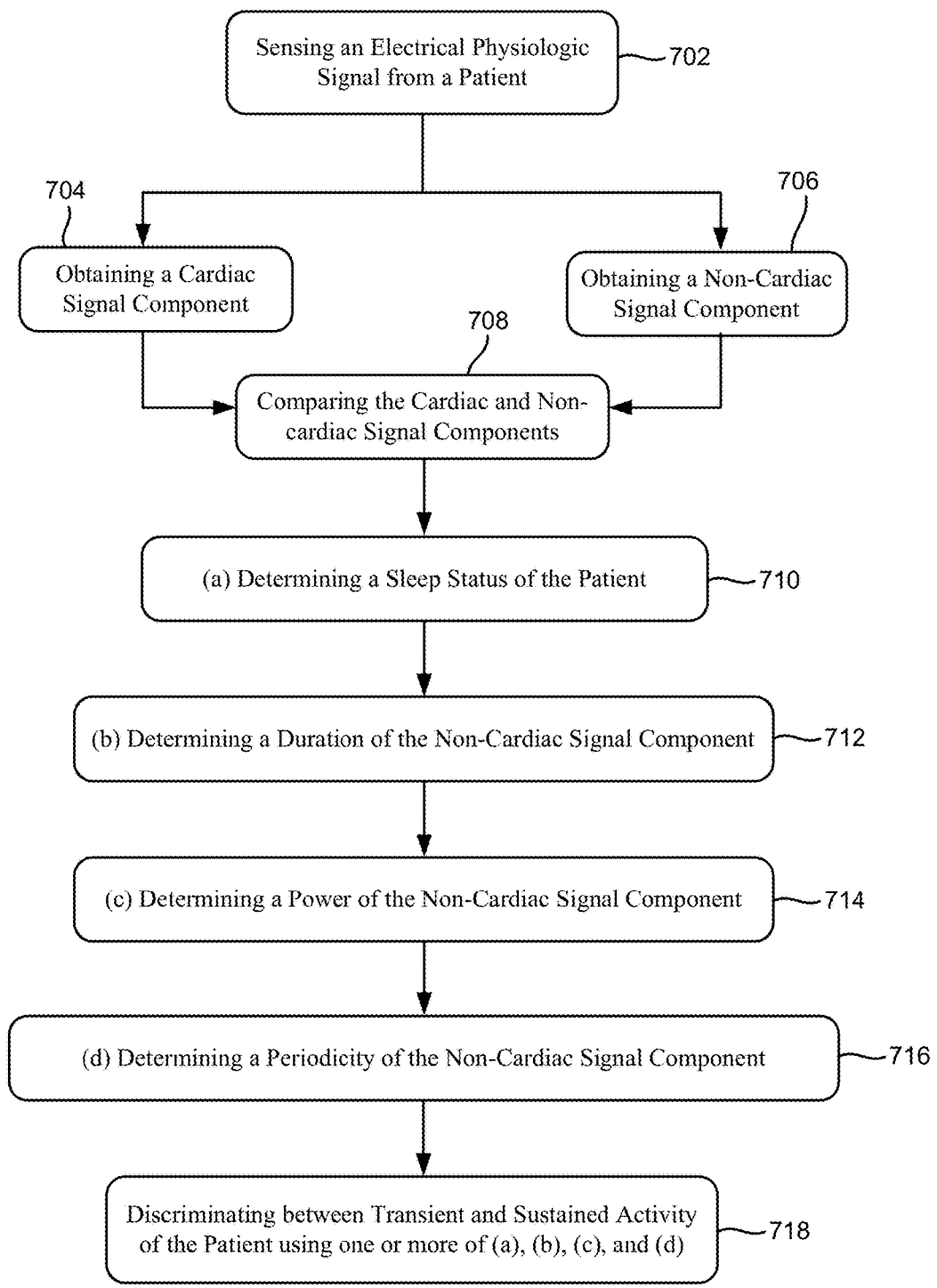
FIG. 7 illustrates a method of assessing patient status in accordance with some embodiments.

FIG. 7 illustrates a method of assessing patient status in accordance with various embodiments. The methodology shown in FIG. 7 involves sensing 702 an electrical physiologic signal from a patient, such as a signal sensed from a subcutaneous, intra-thoracic, or cutaneous location. The sensed electrical physiologic signal is processed to obtain 704 a cardiac signal component and to obtain 706 a non-cardiac signal component. The cardiac signal component may include an ECG signal, for example, and the non-cardiac signal component may include an activity signal indicative of muscle movement, for example. A comparison 708 is performed on the cardiac and non-cardiac signal components, such as comparisons with respective thresholds and/or comparisons between features of the two signal components that reveal interrelationships between the two signal components as discussed previously. Based on the comparison operation 708, the following patient information may be derived: determining 710 a sleep status of the patient (e.g., based on patient activity below a sleep threshold); determining 712 a duration of the non-cardiac signal component (e.g., based on a duration threshold (n seconds or m minutes) distinguishing transient from sustained activity); determining 714 a power of the non-cardiac signal component (e.g., based on a power threshold distinguishing transient (low power) from sustained (high power) activity); and determining 716 a periodicity of the non-cardiac system component (e.g., based on a rhythmicity threshold distinguishing voluntary (periodic) and involuntary (aperiodic). The method shown in FIG. 7 further involves discriminating 718 between transient and sustained (or involuntary and voluntary) activity of the patient using one or more of the determining processes 710, 712, 714, and 716.

Figure 8:
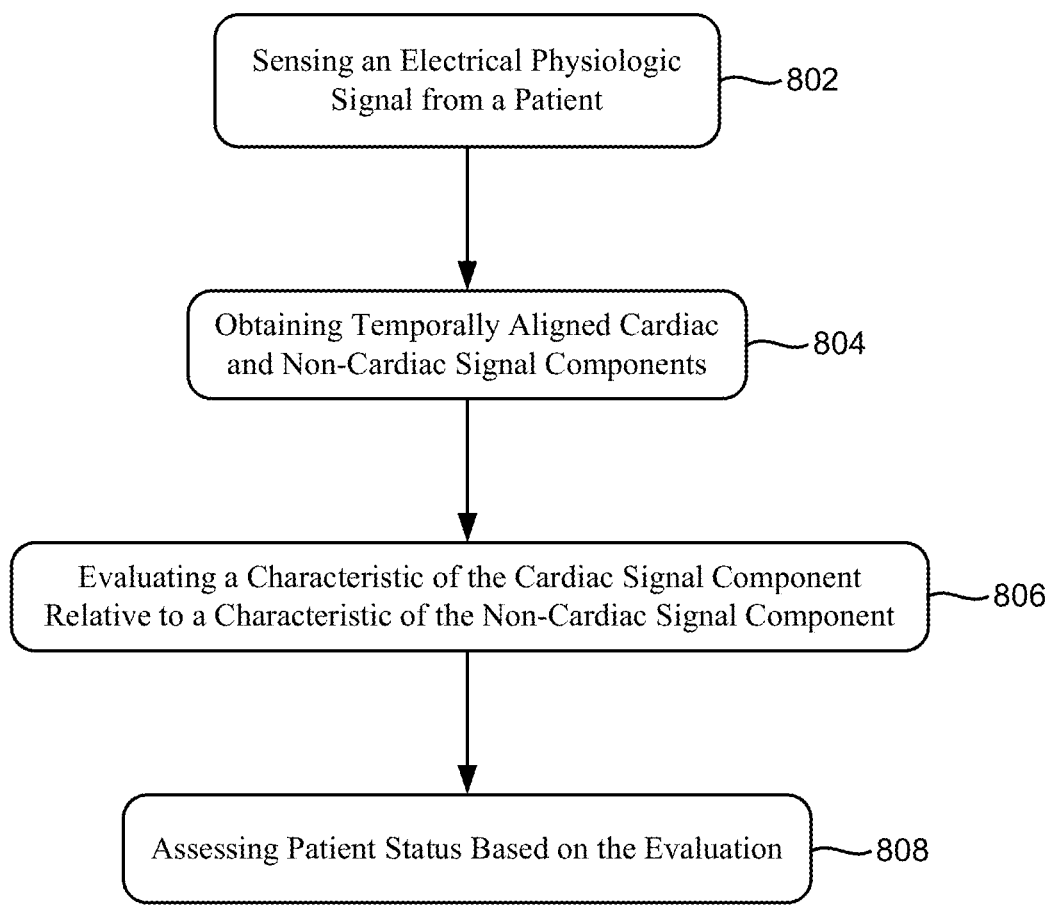
FIG. 8 illustrates a method of assessing patient status in accordance with other embodiments.

FIG. 8 illustrates a method of assessing patient status in accordance with various embodiments. The methodology shown in FIG. 8 involves sensing 802 an electrical physiologic signal from a patient, such as a signal sensed from a subcutaneous, intra-thoracic, or cutaneous location. The sensed electrical physiologic signal is processed to obtain 804 temporally aligned cardiac and non-cardiac signal components. The cardiac signal component may include an ECG signal, for example, and the non-cardiac signal component may include an activity signal indicative of muscle movement, for example. The methodology shown in FIG. 8 further involves evaluating 806 a characteristic of the cardiac signal component relative to a characteristic of the non-cardiac signal component.

The characteristic of the cardiac signal component may include one or more of rate, QRS width, intervals between any of the PQRST features, time-domain characterization, frequency domain characterization, morphology, and any other useful characteristic or combination of characteristics of the cardiac signal component. The characteristic of the non-cardiac signal component may include one or more of intensity, duration, rhythmicity/periodicity, pattern, continuous vs. discontinuous nature (i.e. concatenation), and any other useful characteristic or combination of characteristics of the non-cardiac signal component. Evaluating 806 the cardiac and non-cardiac signal component characteristics may involve one or more of performing a mathematical correlation operation (e.g., feature correlation coefficient computation), a standard deviation operation, regression analysis, dependence analysis, distribution analysis, and any other useful mathematical comparison operation or combination of operations.

Figure 9:
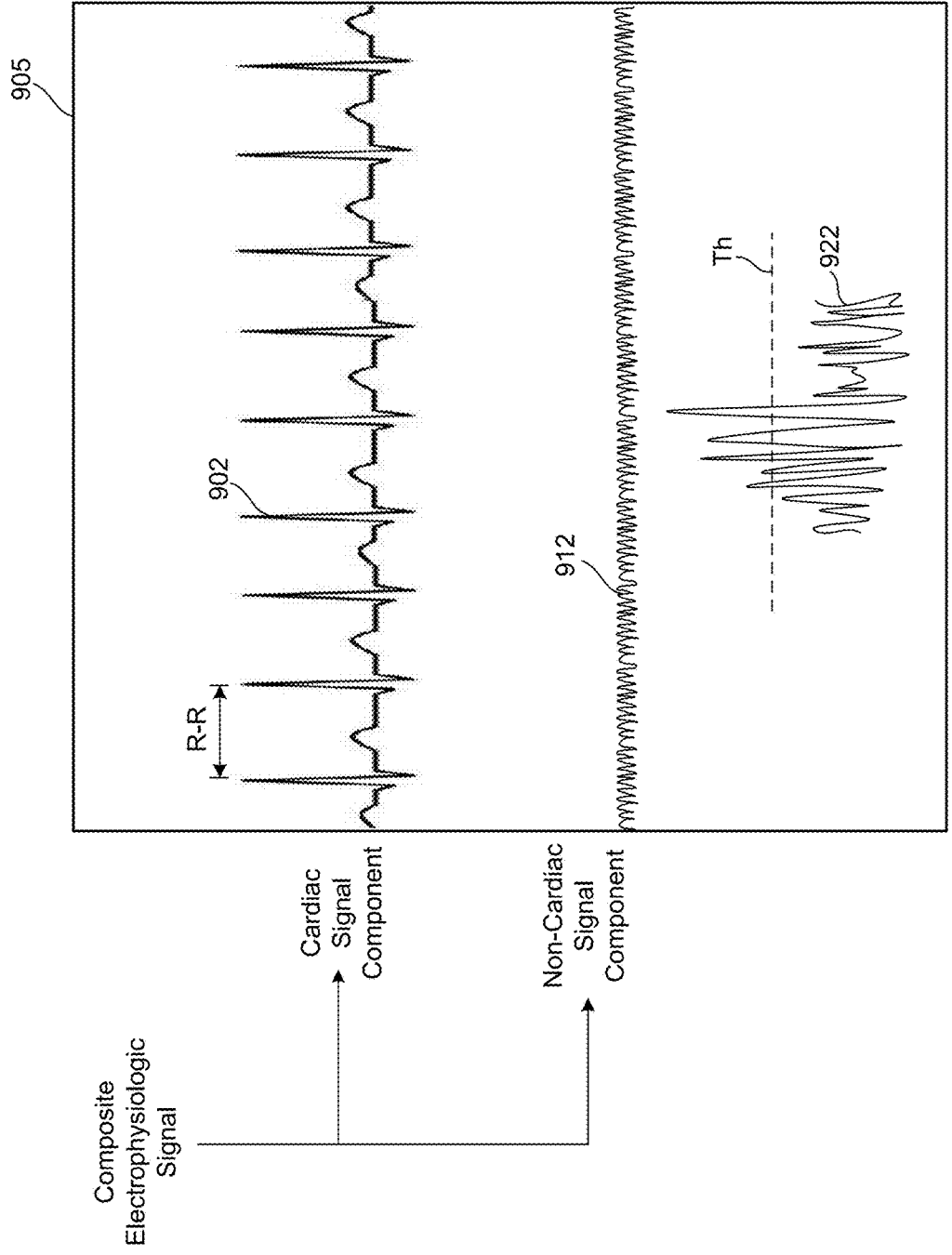
FIG. 9 illustrates a cardiac signal component and a non-cardiac signal component derived from the same composite electrophysiologic signal, which can be used to perform patient monitoring in accordance with various embodiments.

FIG. 9 illustrates a cardiac signal component and a non-cardiac signal component derived from the same composite electrophysiologic signal acquired by a patient monitoring device according to various embodiments. More particularly, FIG. 9 shows a comparison of a cardiac signal component 902 and a non-cardiac signal component 912 derived from the same composite electrophysiologic signal, which can be performed by a patient monitoring device in accordance with various embodiments. It is to be understood that the cardiac and non-cardiac signal components 902 and 912 shown in FIG. 9 and other figures are graphical depictions provided for illustrative purposes, and may not be representative of actual signals. FIG. 9 shows a sampling of the cardiac and non-cardiac signal components 902 and 912 within a detection window 905. The number of signal component samples within the detection window 905 can vary between a few to several hundred or more, depending on how many samples are needed for a particular comparison or analysis operation. In FIG. 9, the cardiac signal component 902 is shown as an ECG signal comprising a sequence of QRS complexes. It is understood that the ECG signal shown in FIG. 9 and other figures can comprise a sequence of PQRST complexes. The non-cardiac signal 912 is shown as an EMG signal comprising a series of high-frequency muscle activity signals. The EMG signal 912 is typically obtained from muscle activity at the location or vicinity of a patient monitoring device affixed to a patient. In the case of an implantable loop recorder, for example, the EMG signal 912 is generally representative of pectoral muscle activity.

The non-cardiac signal component 912, such as an EMG signal, is often a relatively noisy signal. Detection of patient activity is facilitated by comparing the non-cardiac signal component, such as non-cardiac signal component 922 shown in the lower portion of FIG. 9, to a threshold, Th. The threshold, Th, is one that is greater than the noise floor and can be tailored to the activity profile/habits of a specific patient. For example, the threshold, Th, may be set to a lower level for a sedentary patient, and higher for an active patient. The threshold, Th, can be adjusted dynamically by the patient monitoring device based on detection of patient activity over time. For example, a threshold, Th, may initially be set to a lower level following a surgical procedure, then progressively set to higher levels over time in correlation to the patient's rehabilitation. This activity threshold, Th, can be an indicator of the patient's activity level over time. As such, the threshold, Th, can be monitored over time to assess changes in patient activity.

In accordance with various embodiments, a patient monitoring device can be configured to operate on the cardiac and non-cardiac signal components 902 and 912 in various ways. According to some embodiments, each of the signals 902 and 912 can be compared to one or more predetermined thresholds, such as thresholds that indicate relative activity of the patient. Comparison of each individual signal 902 and 912 to its respective threshold or thresholds can reveal the status, such as activity status, of the patient. Evaluating the interplay between the cardiac and non-cardiac signal components 902 and 912 can provide a more comprehensive assessment of patient status.

In the illustrative example shown in FIG. 9, for example, the patient monitoring device can determine that the cardiac signal component 902 within the detection window 905 is relatively stable and rhythmic (e.g., unchanging in duration and morphology), which may indicate the patient is at rest or exercising at a consistent exertion level (e.g., depending on rate threshold testing and evaluation of PQRST features). For example, the cardiac signal component 902 shown in FIG. 9 can be detected by the patient monitoring device as normal sinus rhythm. The patient monitoring device can determine that the non-cardiac signal component 912 depicted within the detection window 905 is relatively stable and consistent, with a relatively unchanging intensity level for example. Various properties of the non-cardiac signal component 912 can be evaluated by the patient monitoring device using one or more of the signal evaluation processes disclosed herein. In the illustrative example shown in FIG. 9, the patient monitoring device can compare the signal components 902 and 912 of the time-aligned signal components 902 and 912) within the detection window 905 to their respective thresholds and, in addition, compare features of each signal component 902 and 912, such as temporally aligned signal features (e.g., compute feature correlation coefficients based on features of the temporally aligned signal components 902 and 912).

By way of example, if the non-cardiac signal component 912 exceeds a predetermined activity threshold, such as threshold 922, and the cardiac signal component 902 is determined to be stable or increasing, the patient monitoring device can conclude that the patient is involved in sustained voluntary activity, such as exercise. If, for example, a comparison between the cardiac and non-cardiac signal components 902 and 912 within the detection window 905 reveals that both signal components 902 and 912 are increasing or decreasing with a similar trajectory, the patient monitoring device can determine that the patient is involved in a compensated heart function activity. If, by way of further example, the non-cardiac signal component 912 does not exceed a predetermined activity threshold and the cardiac signal component 902 is determined to be stable or decreasing somewhat, the patient monitoring device can conclude that the patient is resting or sleeping.

In some embodiments, the patient monitoring device can be programmed to collect physiologic information from a patient on a discontinuous basis. The duration and time separation between adjacent sensing windows can be based on pre-programmed values, on patient-specific factors, and/or adjusted dynamically. For example, physiologic information can be collected several times per day, such as once every minute, every several minutes, every hour, or every several hours according to a pre-programmed schedule. Physiologic information can be collected every several days and/or in response to detecting predetermined events. These discontinuous (non-overlapping) time-separated sensing windows can have the same or different duration (e.g., difference lengths depending on time of day, activity level, cardiac condition, etc.). The comparison operations discussed herein can include comparisons performed on signal components and metrics captured in a multiplicity of time-separated sensing windows. For example, detection of a potentially concerning cardiac condition can trigger opening of one or more addition (i.e., out-of-sequence) sensing windows in order to further assess the potentially concerning cardiac condition. The patient monitoring device can evaluate the cardiac and non-cardiac signal information acquired for each of these sensing windows to provide a more accurate assessment of the potentially concerning cardiac condition of the patient. The duration of each detection window (e.g., window 905 shown in FIG. 9) can be the same length as its associated sensing window or be of shorter duration.

Figure 10:
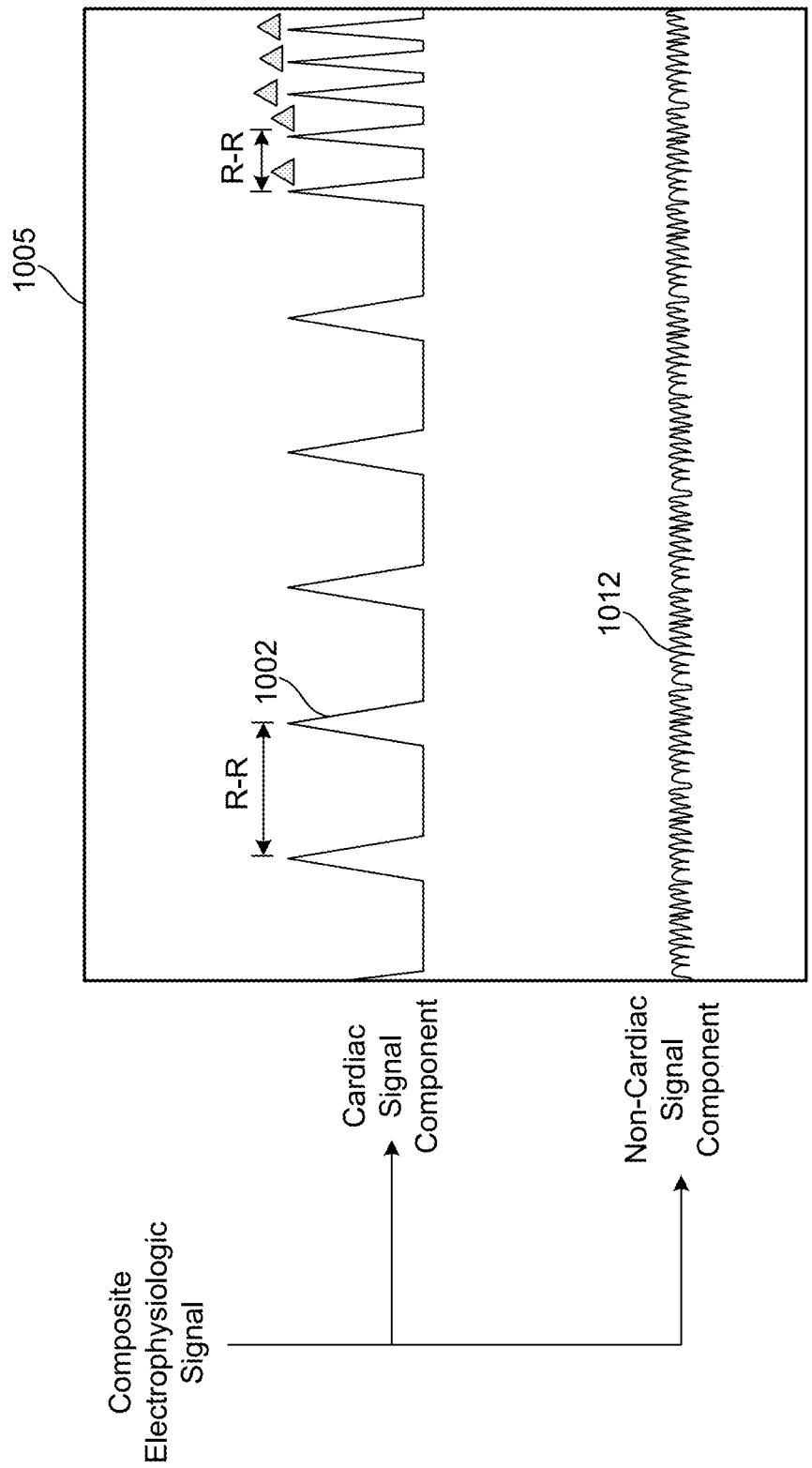
FIG. 10 illustrates a cardiac signal component and a non-cardiac signal component derived from the same composite electrophysiologic signal, which can be used to perform patient monitoring in accordance with various embodiments.

FIG. 10 shows a comparison of a representative cardiac signal component 1002 and a non-cardiac signal component 1012 derived from the same composite electrophysiologic signal, which can be operated on by a patient monitoring device in accordance with various embodiments. In the illustrative example shown in FIG. 10, the cardiac signal component 1002 (depicted as a sequence of simplified QRS complexes) within a detection window 1005 indicates that the patient's heart rate is increasing over the time. This increase in patient heart rate is shown as a progressive decrease in R-R cycle length. While the patient's heart rate is determined to be increasing for the cardiac signal component sample 1002 shown in FIG. 10, the non-cardiac signal component 1012 indicates stable, non-increasing muscle activity over the duration of the detection window 1005. In this illustrative scenario, the trajectories of the two signals 1002 and 1012 within the detection window 1005 may be inconsistent with normal or healthy patient activity.

For example, an increasing heart rate as shown in FIG. 10 should be accompanied by an increase in a pectoral muscle activity due to patient movement/exercise. Based on a presence of an increasingly faster cardiac signal 1002 and absence of a corresponding increasing muscle activity signal 1012 within the detection window 1005, the patient monitoring device can determine that the patient is experiencing an uncompensated arrhythmia. In response, the patient monitoring device can generate a warning, which can be transmitted to an external device or system, thereby alerting the patient, caregiver or a clinician to a potentially dangerous patient situation. According to some embodiments, an ECG waveform (e.g., strip) is generated in response to detecting an adverse patient condition. The ECG strip can include the non-cardiac signal waveform. The ECG strip can be annotated using indicia or a maker (e.g., triangles) to indicate the adverse patient condition. For example, the ECG strip can be annotated with a marker to indicate the point in time of disharmony or dyssynchrony between the cardiac and muscle activity signals 1002 and 1012 (e.g., one signal indicating involuntary activity while the other signal indicates voluntary activity).

Figure 11:
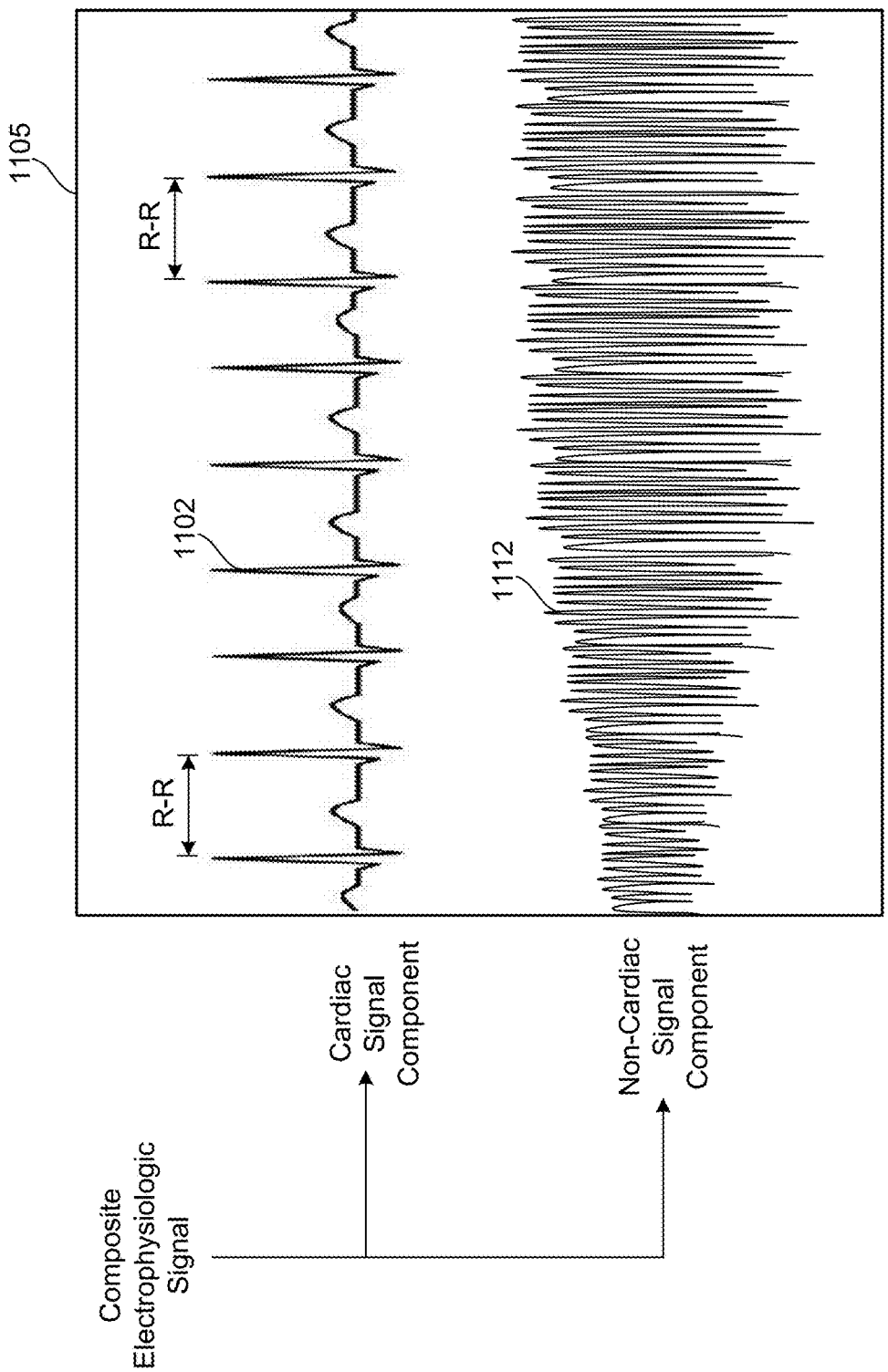
FIG. 11 illustrates a cardiac signal component and a non-cardiac signal component derived from the same composite electrophysiologic signal, which can be used to perform patient monitoring in accordance with various embodiments.

FIG. 11 shows a comparison of a cardiac signal component 1102 and a non-cardiac signal component 1112 derived from the same composite electrophysiologic signal that can be performed by a patient monitoring device in accordance with various embodiments. In the illustrative example shown in FIG. 11, the cardiac signal component 1102 within a detection window 1105 indicates that the patient's heart rate is relatively stable (e.g., generally unchanging in duration and morphology) over the duration of the cardiac signal component sample shown in FIG. 11 (e.g., normal sinus rhythm). The relative stability of the patient heart rate can be seen in FIG. 11 by an R-R interval of relatively consistent duration. While the patient's heart rate is relatively stable over the time sample shown in FIG. 11, the non-cardiac signal component 1112 indicates increasing muscle activity over the same time period. In this illustrative scenario, the trajectories of the two signals 1102 and 1112 within the detection window 1105 may be inconsistent with normal or healthy patient activity. For example, and assuming that a threshold comparison of the cardiac signal component 1102 indicates a low patient heart rate, the presence of low patient heart rate and high activity intensity indicated by the non-cardiac signal component 1112 within the detection window 1105 can indicate an inadequate cardiac chronotropic function or other pathological condition. In the case of epilepsy, for example, an epileptic seizure will result in periodic high intensity bursts of the non-cardiac signal 1112 rather than a gradual ramp as is depicted for illustrative purposes in FIG. 11.

Figure 12:
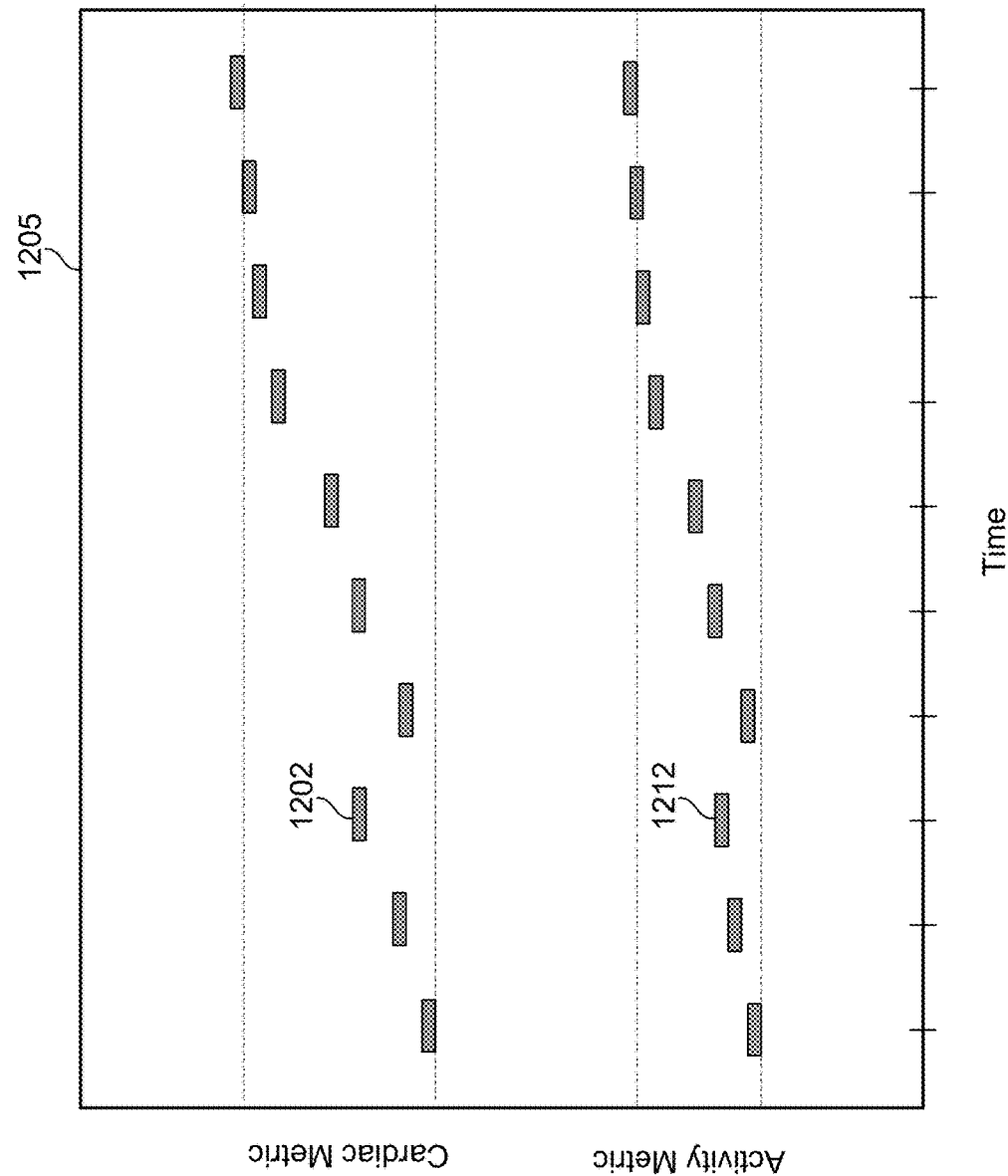
FIG. 12 is a graphical showing of cardiac metrics and activity metrics derived from cardiac and non-cardiac signal components of the same composite electrophysiologic signal in accordance with various embodiments.

FIG. 12 is a graphical showing of cardiac metrics 1202 and activity metrics 1212 derived from cardiac and non-cardiac signal components of the same composite electrophysiologic signal in accordance with various embodiments. In the illustrative example shown in FIG. 12, the cardiac metric can be a measure of heart rate, QRS width, intervals between any of the PQRST features, time-domain characterization, frequency domain characterization, morphology, and any other useful characteristic or combination of characteristics of the cardiac signal component. The activity metric can be a measure of intensity, duration, power, rhythmicity/periodicity, pattern, continuous vs. discontinuous nature (i.e. concatenation), and any other useful characteristic or combination of characteristics of the non-cardiac signal component. Although FIG. 12, as well as FIGS. 13 and 14 graphically show a single cardiac metric in temporal alignment with a single activity metric within a detection window 1205, it is understood that a multiplicity of disparate temporally related cardiac and activity metrics can be evaluated by a patient monitoring device according to various embodiments.

In FIG. 12, a patient monitoring device can compare the cardiac metric 1202 and the activity metric 1212 within the detection window 1205 to their respective threshold or thresholds to determine information about each metric individually. The patient monitoring device can also perform an evaluation of a multiplicity of temporally aligned metrics to provide a more thorough assessment of patient status. A metric comparison operation performed by the patient monitoring device according to various embodiments can involve one or more of performing a correlation operation (e.g., feature correlation coefficient computation), a standard deviation operation, regression analysis, dependence analysis, distribution analysis, and any other useful mathematical comparison operation or combination of operations. In FIG. 12, the cardiac metric 1202 is shown in time-alignment with respect to the activity metric 1212, which is readily achievable since the two metrics are derived from the same electrophysiologic signal. A time-wise comparison of the intensity or magnitude of the metrics 1202 and 1212 shown in FIG. 12, for example, reveals that the metrics 1202 and 1212 track each other fairly consistently. The patient monitoring device can determine that the interplay between the cardiac and activity metrics 1202 and 1212 within the detection window 1205 indicates normal patient status.

Figure 13:
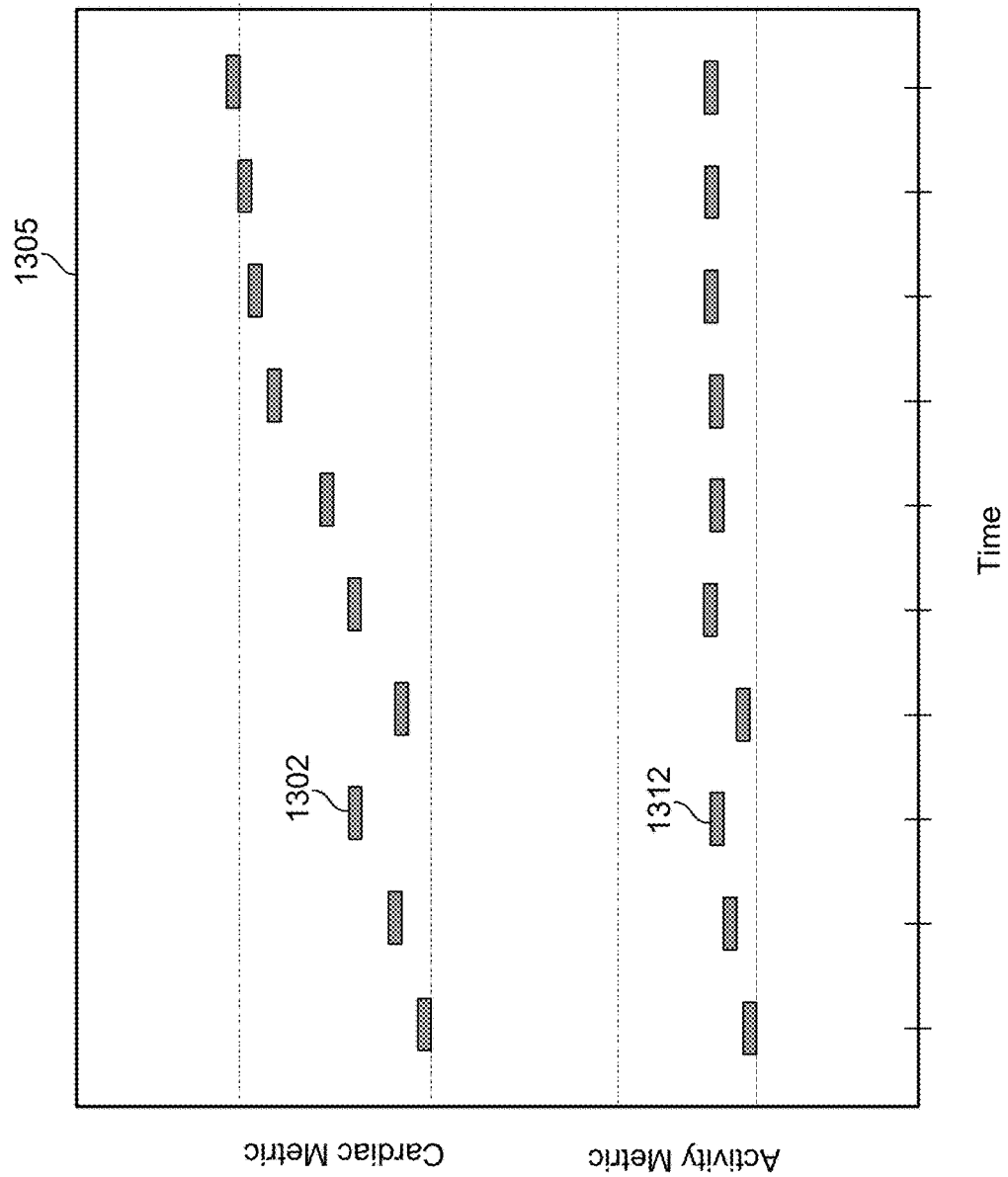
FIG. 13 is a graphical showing of cardiac metrics and activity metrics derived from cardiac and non-cardiac signal components of the same composite electrophysiologic signal in accordance with various embodiments.
Figure 14:
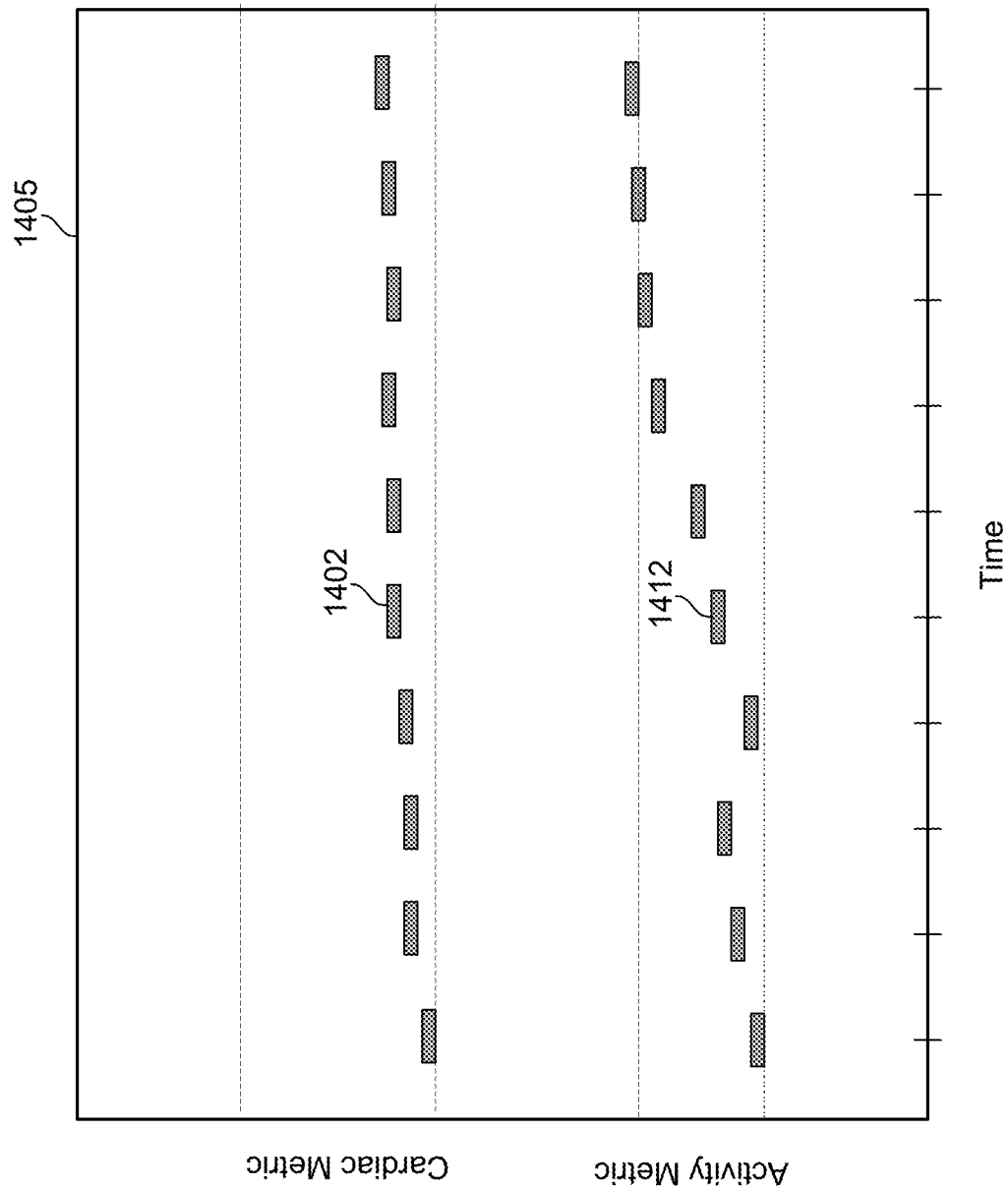
FIG. 14 is a graphical showing of cardiac metrics and activity metrics derived from cardiac and non-cardiac signal components of the same composite electrophysiologic signal in accordance with various embodiments.

In FIG. 13, a cardiac metric 1302 is generally increasing with time for the sample within the detection window 1305, while an activity metric 1312 remains relatively steady. The patient monitoring device can determine the interplay between the cardiac and activity metrics 1302 and 1312 within the detection window 1305 to indicate an abnormal patient status, such as uncompensated arrhythmia. In FIG. 14, a cardiac metric 1402 is relatively stable with time within the detection window 1405, while an activity metric 1412 is generally increasing over the same time sample. The patient monitoring device can determine that the interplay between the cardiac and activity metrics 1402 and 1412 within the detection window 1405 indicates an abnormal patient status, such as inadequate cardiac chronotropic function or other adverse condition.

According to some embodiments, one or both of the cardiac and activity metrics shown in FIGS. 12-14 are adjustable thresholds that can be dynamically changed during patient monitoring by the patient monitoring device operating in a closed-loop manner. In some embodiments, the adjustable thresholds operative in a patient monitoring device are dynamically computed during patient monitoring by an external system, which can be configured to change the adjustable thresholds of the patient monitoring device remotely. In other embodiments, the adjustable thresholds operative in a patient monitoring device are modifiable by a clinician during patient monitoring via an external system (e.g., open-loop or quasi open loop operation). The adjustable thresholds of the patient monitoring device can be updated to the algorithmically computed (e.g., closed-loop) settings or clinician (e.g., open-loop) settings via the external system.

Figure 15:
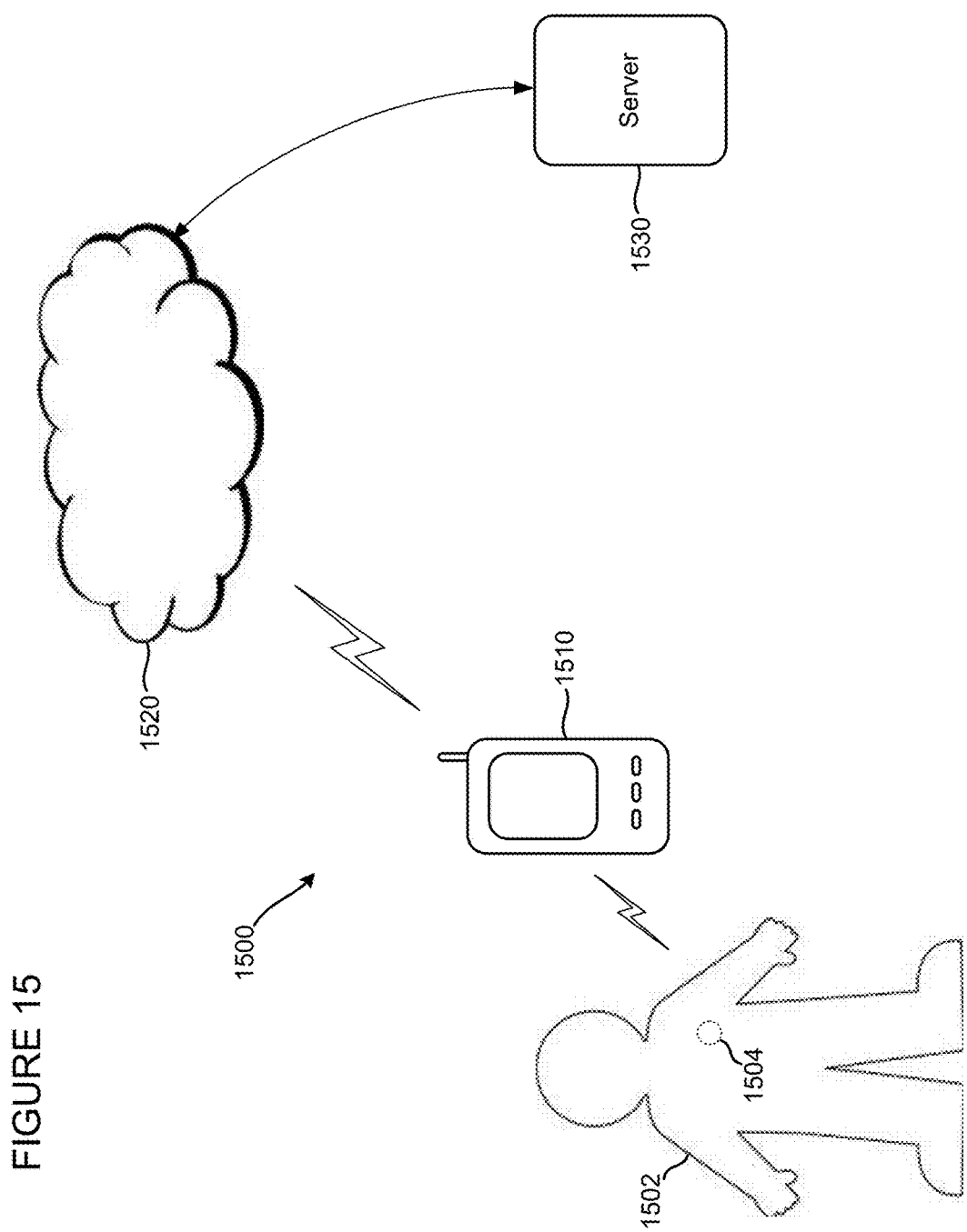
FIG. 15 is a diagram of a representative system for assessing a patient in accordance with various embodiments.

A patient monitoring device of a type disclosed herein can be embodied in an implantable device (e.g., subcutaneous extra-thoracic device, intra-thoracic device), a cutaneous patient-external device, or a hybrid device having both patient-internal and patient-external components. A patient monitoring device of a type disclosed herein can be incorporated in a variety of system implementations, a representative example of which is shown in FIG. 15. The system 1500 includes a patient monitoring device 1504 implanted in a body of a patient 1502. The device 1504 may correspond to any of the patient monitoring devices disclosed herein. When implanted, the device 1504 may collect physiological data from the patient 1502. A handheld computing device 1510 may be programmed to communicate wirelessly (e.g., transmit or receive data via radio frequency telemetry) with the implantable device 1504. In some implementations, an external charging device (not shown) may be used to periodically recharge a battery of the implantable device 1504, though the device 1504 may alternatively use a single-use battery in some implementations.

In various implementations, the patient 1502 may use the handheld device 1510 to manually initiate data collection by the device 1504 (e.g., initiate ECG signal sensing and recording). For example, if the patient 1502 feels lightheaded or feels palpitations in her chest, she may press a button on the handheld device 1510, and the handheld device 1510 may wirelessly command the device 1504 to record and store physiologic data. The device 1504 may also record a physiologic signal when it determines that such recordation may provide useful information. For example, the device 1504 may monitor a physiologic parameter (e.g., heart rate), and may record an ECG signal based on predetermined characteristics of the physiologic parameter. In some implementations, the device 1504 may periodically record sensed physiologic information according to a predetermined schedule. For example, the device may record a strip of data (e.g., covering a predetermined number of heart beats or having a predetermined strip duration or length) once every minute, every several minutes, every hour, every several hours, every day, every several days, etc.

The device 1504 may periodically transmit collected data to the handheld device 1510, such as every few hours or once per day, for example. In some implementations, the device 1504 may transmit sensed data in real time to the handheld device 1510, and the handheld device 1510 may store the data in internal memory or display the data as a waveform or otherwise on a display screen of the handheld device 1510. The handheld device 1510 is configured to wirelessly communicate with the cloud 1520 (e.g., the Internet) via a cellular or Wi-Fi connection, and to establish a connection with a remote server 1530. The handheld device 1510 may send and receive data to/from the server 1530. In some embodiments, the handheld device 1510 may transmit data through the cloud 1520 and to the remote server 1530, where the data may be processed and analyzed automatically (e.g., algorithmically by the server 1530) and/or by a physician or a health care provider. Thresholds can be computed at the server 1530 and transmitted to handheld device 1510 for upload to the device 1504. In some implementations, data analysis may occur within one or both of the device 1504 and the handheld device 1510 (or in a distributed manner between two or more of these components). Data analysis can include detection of cardiac, musculature, neural, and sleep anomalies based on the collected data and trending of such detection data. Data analysis can also include monitoring of a disease status of the patient 1502.

Figure 16:
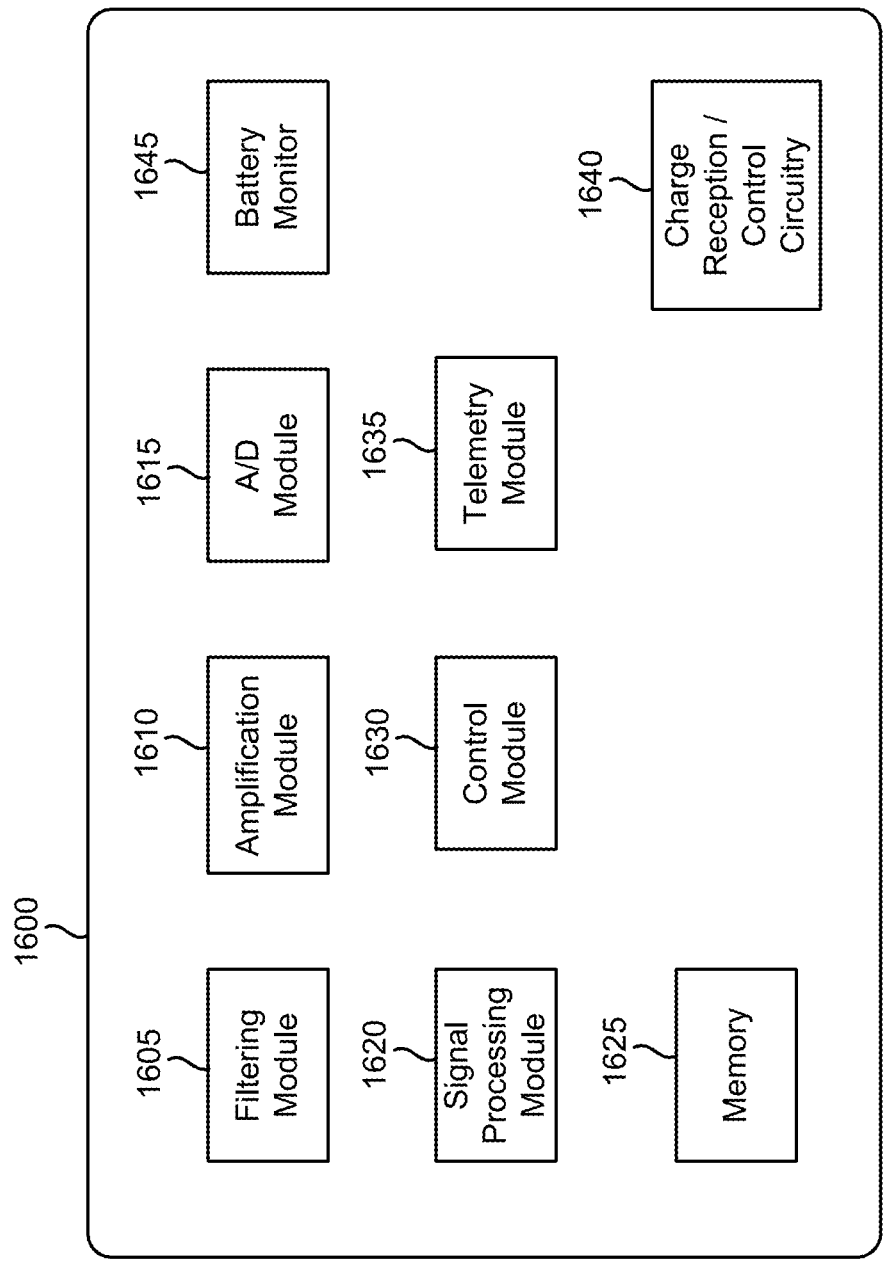
FIG. 16 is a block diagram of circuitry that may be included in implementations of a system for assessing a patient in accordance with various embodiments.

FIG. 16 is a block diagram of circuitry 1600 that may be included in implementations of a patient monitoring device disclosed herein. In some implementations, the circuitry 1600 or a portion thereof may be included in the electronics circuitry shown in various preceding figures. Components or modules may be combined or separated as desired, and may be positioned in one or more portions of the implanted device. A filtering module 1605 may receive a sensed physiologic signal and appropriately filter the signal to remove unwanted noise or to pare the received signal to information in a desired frequency range, or above or below a desired frequency threshold. An amplification module 1610 may amplify the received signal for processing, and an analog-to-digital converter 1615 may convert the analog signal to a digital signal. The digital signal may be stored directly into memory 1625, or may first be processed by a signal processing module 1620. Signal processing module 1620 may include functions to extract information from the measured signal, or to compress the measured signal to reduce the volume of data to store and transmit. Memory 1625 may include both volatile and non-volatile memory, according to various implementations, and may additionally store instructions that can be executed by a processor or logic device to perform specified actions.

A control module 1630 may provide overall device control, and may include one or more processors that can execute instructions and in response perform actions. A telemetry module 1635 may be used, in conjunction with the telemetry antenna, for communication with an external device. Charge reception/control circuitry 1640 may optionally be used in implementations that include a rechargeable battery to control reception of charge energy over a charge reception apparatus and coordinate recharging of the battery. A battery monitoring module 1645 may provide one or more of controlling the charge current/voltage as appropriate for the type of battery, providing data that can be transmitted to a charger during charging to control and terminate charge time, assess a state of the battery from charge to depletion via voltage, impedance, charge-counting or other means, provide data to communicate to an external device for feedback as to when to charge or if an early charge is required. For simplicity, connections between the various modules are not shown in FIG. 16.

CONCLUSION

The above description is intended to be illustrative, and not restrictive. For example, the above-described examples (or one or more aspects thereof) may be used in combination with each other. Other examples may be used, such as by one of ordinary skill in the art upon reviewing the above description. Also, in the above Detailed Description, various features may be grouped together to streamline the disclosure. This should not be interpreted as intending that an unclaimed disclosed feature is essential. Rather, inventive subject matter may lie in less than all features of a particular disclosed example.

What is claimed is:

1. A method comprising:
   sensing, from a patient, an electrical physiologic signal between a single electrode pair;
   obtaining, using detection circuitry, a cardiac signal component from the electrical physiologic signal;
   obtaining, using the detection circuitry, a non-cardiac signal component from the electrical physiologic signal;

comparing, using a processor, the cardiac and non-cardiac signal components to respective thresholds established for the patient;

detecting, using the processor, patient activity using the cardiac signal component;

detecting, using the processor, patient activity using the non-cardiac signal component;

determining, using the processor, whether the patient activity detected using the cardiac signal component corresponds to voluntary classified activity or involuntary classified activity of the patient and whether the patient activity detected using the non-cardiac signal component corresponds to voluntary classified activity or involuntary classified activity of the patient;

detecting, using the processor, an adverse patient condition in response to detecting that one of the cardiac and non-cardiac signal components indicates patient voluntary classified activity and the other of the cardiac and non-cardiac signal components indicates patient involuntary classified activity based on the comparison and temporal alignment of the cardiac signal component relative to the non-cardiac signal component; and generating, by the processor, an output comprising the cardiac signal component, the non-cardiac signal component, and an indicator of dyssynchrony between the cardiac and non-cardiac signal components indicative of the detected adverse patient condition.

2. The method of claim 1, wherein, for the non-cardiac signal component:
voluntary classified activity of the patient comprises sustained activity of the patient; and
involuntary classified activity of the patient comprises transient activity of the patient.

3. The method of claim 1, wherein detecting the adverse patient condition further comprises performing a mathematical correlation between the temporally aligned cardiac and non-cardiac signal components.

4. The method of claim 1, wherein detecting the adverse patient condition further comprises:
comparing a trajectory of the cardiac signal component to a trajectory of the non-cardiac signal component during a detection window.

5. The method of claim 1, further comprising:
determining a sleep status of the patient using the non-cardiac signal component or the cardiac signal component;
wherein determining whether the detected patient activity corresponds to voluntary classified activity or involuntary classified activity of the patient is based at least in part on the sleep status of the patient.

6. The method of claim 1, further comprising:
determining a duration of the non-cardiac signal component;
wherein determining whether the detected patient activity corresponds to voluntary classified activity or involuntary classified activity of the patient is based at least in part on the duration of the non-cardiac signal component.

7. The method of claim 1, further comprising:
determining a power of the non-cardiac signal component;
wherein determining whether the detected patient activity corresponds to voluntary classified activity or involuntary classified activity of the patient is based at least in part on the power of the non-cardiac signal component.

8. The method of claim 1, further comprising:
determining a periodicity of the non-cardiac signal component;
wherein determining whether the detected patient activity corresponds to voluntary classified activity or involuntary classified activity of the patient is based at least in part on the periodicity of the non-cardiac signal component.

9. The method of claim 1, wherein the adverse patient condition is an indication of uncompensated cardiac rhythms.

10. The method of claim 1, wherein the adverse patient condition is an indication of an episode of epileptic seizure.

11. The method of claim 1, wherein:
the method comprises adjusting the threshold of the non-cardiac signal component over time based on changes in patient activity over time.

12. The method of claim 11, comprising detecting a change in patient status based on a change in the thresholds.

13. The method of claim 1, wherein the indicator of dyssynchrony comprises a marker that indicates a point in time of dyssynchrony between the cardiac and non-cardiac signal components indicative of the detected adverse patient condition.

14. A medical device comprising:
a housing;
an electrode arrangement coupled to the housing and configured to sense an electrical physiologic signal from a patient;
detection circuitry coupled to the electrode arrangement and configured to obtain a cardiac signal component and a non-cardiac signal component from the electrical physiologic signal;
an output device; and
a processor coupled to the detection circuitry and the output device, the processor configured to:
detect patient activity using the non-cardiac signal component and to detect patient activity using the cardiac signal component;
determine whether the patient activity detected using the cardiac signal component corresponds to voluntary classified activity or involuntary classified activity of the patient and whether the patient activity detected using the non-cardiac signal component corresponds to voluntary classified activity or involuntary classified activity of the patient;
detect an adverse patient condition in response to detecting that one of the cardiac and non-cardiac signal components indicates patient voluntary classified activity and the other of the cardiac and non-cardiac signal components indicates patient involuntary classified activity; and
cooperate with the output device to generate an output comprising the cardiac signal component, the non-cardiac signal component, and an indicator that indicates dyssynchrony between the cardiac and non-cardiac signal components indicative of the detected adverse patient condition.

15. The device of claim 14, wherein, for the non-cardiac signal component:
voluntary classified activity of the patient comprises sustained activity of the patient; and
involuntary classified activity of the patient comprises transient activity of the patient.

16. The device of claim 14, wherein the processor is configured to perform a mathematical correlation between the temporally aligned cardiac and non-cardiac signal components.

17. The device of claim 14, wherein:
the detection circuitry is configured to compare the non-cardiac signal component to a threshold, and
the processor is configured to adjust the threshold over time based on changes in patient activity over time.

18. The device of claim 17, wherein the processor is configured to detect a change in patient status based on a change in the threshold.

19. The device of claim 14, wherein the indicator of dyssynchrony comprises a marker that indicates a point in time of dyssynchrony between the cardiac and non-cardiac signal components indicative of the detected adverse patient condition.

* * * * *